US011034994B2

(12) United States Patent
Delikatny et al.

(10) Patent No.: US 11,034,994 B2
(45) Date of Patent: Jun. 15, 2021

(54) IN VIVO DETECTION OF PHOSPHOLIPASE ACTIVATION

(71) Applicant: THE TRUSTEES OF THE UNIVERSITY OF PENNSYLVANIA, Philadelphia, PA (US)

(72) Inventors: Edward J. Delikatny, Havertown, PA (US); Anatoliy V. Popov, Philadelphia, PA (US); Gang Zheng, Toronto (CA); Theresa Mawn, Philadelphia, PA (US)

(73) Assignee: THE TRUSTEES OF THE UNIVERSITY OF PENNSYLVANIA, Philadelphia, PA (US)

(*) Notice: Subject to any disclaimer, the term of this patent is extended or adjusted under 35 U.S.C. 154(b) by 0 days.

(21) Appl. No.: 15/967,216

(22) Filed: Apr. 30, 2018

(65) Prior Publication Data
US 2018/0245129 A1 Aug. 30, 2018

Related U.S. Application Data

(62) Division of application No. 12/920,451, filed as application No. PCT/US2009/035822 on Mar. 3, 2009, now Pat. No. 9,957,546.

(60) Provisional application No. 61/064,404, filed on Mar. 4, 2008.

(51) Int. Cl.
*A61B 5/00* (2006.01)
*A61B 8/00* (2006.01)
*A61B 10/00* (2006.01)
*C12Q 1/61* (2006.01)
*A61K 49/00* (2006.01)
*G01N 33/50* (2006.01)
*G01N 33/542* (2006.01)
*G01N 33/574* (2006.01)
*A61K 41/00* (2020.01)

(52) U.S. Cl.
CPC ............ *C12Q 1/61* (2013.01); *A61K 49/0036* (2013.01); *G01N 33/5011* (2013.01); *G01N 33/542* (2013.01); *G01N 33/57484* (2013.01); *A61K 41/0071* (2013.01); *A61K 49/0017* (2013.01); *A61K 49/0032* (2013.01)

(58) Field of Classification Search
None
See application file for complete search history.

(56) References Cited

U.S. PATENT DOCUMENTS

| 6,180,596 B1 | 1/2001 | Tsao |
| 7,301,043 B2 | 11/2007 | Deigner et al. |
| 2002/0038199 A1 | 3/2002 | Blemel |
| 2002/0049986 A1 | 4/2002 | Farber et al. |
| 2002/0131970 A1 | 9/2002 | Altieri et al. |
| 2002/0162124 A1 | 10/2002 | Farber et al. |
| 2003/0135869 A1 | 7/2003 | Farber et al. |
| 2003/0219849 A1 | 11/2003 | Tsao et al. |
| 2004/0219616 A1 | 11/2004 | Seery et al. |
| 2005/0026235 A1 | 2/2005 | Graham |
| 2005/0064532 A1 | 3/2005 | Deigner et al. |
| 2005/0244891 A1 | 11/2005 | Graham et al. |
| 2005/0244907 A1 | 11/2005 | Graham et al. |
| 2007/0042398 A1* | 2/2007 | Peng .................. G01N 33/532 435/6.12 |

FOREIGN PATENT DOCUMENTS

| WO | WO 1995/032181 | 11/1995 |
| WO | WO 2005/048944 A2 | 6/2005 |
| WO | WO 2005/080407 A1 | 9/2005 |

OTHER PUBLICATIONS

Mawn et al. (Mol. Imaging 5, 315, 2006).*
Mawn et al.: Design and Characterization of an Enzyme-Activated Near-Infrared Probe Highly Specific to Phosphatidylcholine-Specific Phospholipase. Mol Imaging, 5, 315 (2006).
Steflova et al. Using molecular beacons for cancer imaging and treatment. Fronteirs in Bioscience 2007, 12:4709-4721, p. 4711, col. 2, In 8-11: pp. 4713, col. 1, In 13-14; p. 4714, col. 1, para 3, In 1-2; p. 4716, col. 1, in 12; p. 4717, col. 2, para 2, In 6-7.
Farber et al. "Characterization of Ca21-dependent Phospholipase A2 Activity during Zebrafish Embryogenesis", The Journal of Biological Chemistry vol. 274, No. 27, Issue of Jul. 2, pp. 19338-19346, 1999.
Farber et al. "Genetic Analysis of Digestive Physiology Using Fluorescent Phospholipid Reporters", Science vol. 292, May 18, 2001.
Hendrickson et al. "Intramoleculary Quenched BODIPY-Labeled Phospholipid Analogs in Phospholipase A2 and Platelet-Activating Factor Acetyihydrolase Assays and in Vivo Fluorescence Imaging", Analytical Biochemistry 276, 27±35 (1999).
International Search Report for PCT Application No. PCT/US09/35822 dated Jun. 1, 2009.
Mawn et al. Design and characterization of an enzyme-activated near-infrared probe highly specific to phosphatidylcholine-specific phospholipase C. Frontiers in Metabolic, Molecular and Clinical Imaging, ISMRM Workshop on MR of Cancer, Pocono Manor, PA, Oct. 2006.
Mawn et al, "Design and characterization of an enzyme-activated near-infrared probe highly specific to phosphatidylcholine-specific phospholipase C", Cruising into Molecular Imaging, ISMRM Workshop on Molecular Imaging, Galveston TX, Feb. 2007.
Molecular Probes, "Product Information: Phospholipids" May 13, 2003.
Terao et al. "Singlet molecular oxygen1guenching activity of carotenoids: relevance to protection of the skin from photoagino", J. Ciin, Biochem. Nutr., Jan. 2011, vol. 48 No. 1, pp. 57-62.

* cited by examiner

Primary Examiner — Michael G. Hartley
Assistant Examiner — Melissa J Perreira
(74) Attorney, Agent, or Firm — Mark S. Cohen; Pearl Cohen Zedek Latzer Baratz LLP

(57) ABSTRACT

The present invention is directed to a phospholipid-based NIR molecular beacon, having a phospholipid moiety; with an NIR fluorophore moiety covalently linked to a phospholipid glycerol backbone and a quencher moiety covalently linked to the phospholipid glycerol backbone. Additionally, provided herein is methods of analyzing a sample for the presence of a phospholipase and methods of identifying the activity of a phospholipase in vivo utilizing phospholipid-based NIR molecular beacon.

10 Claims, 16 Drawing Sheets

NIRF1 (Pyro)

NIRF2 (Bchl)

IN VIVO DETECTION OF PHOSPHOLIPASE ACTIVATION

GOVERNMENT INTEREST STATEMENT

This invention was made with government support under grant number EB002537 awarded by the National Institutes of Health. The government has certain rights in the invention.

FIELD OF THE INVENTION

Provided herein are compounds, compositions, and methods for detection of phospholipases in vivo and their use.

BACKGROUND OF THE INVENTION

Over the past decade, magnetic resonance spectroscopy (MRS) studies have consistently revealed the presence of elevated levels of phosphocholine (PCho) and total choline in various types of cancer cells and solid tumors. It has been shown that PCho levels are correlated with the degree of malignancy in cancer, and that PCho levels decrease in response to successful chemotherapeutic treatment or gene silencing by siRNA. Increased expression levels of PCho have been associated with the up-regulation of choline transport and choline kinase activity, as well as increased catabolism mediated by elevations in phospholipase C (PLC) activity. However the relative contributions of the anabolic and catabolic pathways of PCho formation have not been determined.

Accordingly, a need exists in the art for a reliable method to monitor the activation of phospholipase in vivo.

SUMMARY OF THE INVENTION

In one embodiment, provided herein is a phospholipid-based near infrared (NIR) molecular beacon comprising a phospholipid moiety, a first fluorophore moiety covalently linked to the glycerol backbone of said phospholipid either directly or via a linker, wherein said first fluorophore moiety is an NIR fluorophore moiety; and a quencher moiety covalently linked to said phospholipid glycerol backbone either directly or via a linker, wherein a change in fluorescence of said NIR fluorophore is detectable upon an enzymatic cleavage of said phospholipid.

In another embodiment, the present invention provides a method of analyzing a sample for the presence of a phospholipase, the method comprising: contacting a sample suspected of containing a phospholipase with a phospholipid-based near infrared (NIR) molecular beacon comprising a phospholipid moiety; a first fluorophore moiety covalently linked to the glycerol backbone of said phospholipid either directly or via a linker, wherein said first fluorophore moiety is a NIR fluorophore moiety; and a quencher moiety, wherein a change in fluorescence of said NIR fluorophore is detectable upon an enzymatic cleavage of said phospholipid beacon; and detecting the fluorescence of said NIR fluorophore moiety as a function of time, wherein an increase in fluorescence as a function of time correlates with the presence of the phospholipase in the sample.

In another embodiment, the present invention provides a method of monitoring the activity of a phospholipase in vivo, comprising the steps of: exposing a tissue to a molecular beacon comprising a phospholipid moiety; a first fluorophore moiety covalently linked to the glycerol backbone of said phospholipid either directly or via a linker, wherein said first fluorophore moiety is a near infrared (NIR) fluorophore moiety; and a quencher moiety, wherein a change in fluorescence of said NIR fluorophore is detectable upon an enzymatic cleavage of said phospholipid beacon; and detecting the fluorescence of said fluorophore moiety as a function of time, wherein an increase in the quantity or rate of accumulation of fluorescence as compared to a control reaction identifies the activity of the phospholipase.

In another embodiment, the present invention provides a method of identifying a modulator of a phospholipase in vivo, comprising the steps of: contacting a tissue comprising a phospholipase with a) a molecular beacon comprising a phospholipid moiety; a first fluorophore moiety covalently linked to the glycerol backbone of said phospholipid either directly or via a linker, wherein said first fluorophore moiety is a near infrared (NIR) fluorophore moiety; and a quencher moiety, wherein a change in fluorescence of said NIR fluorophore is detectable upon an enzymatic cleavage of said phospholipid beacon; and b) a candidate modulator compound under conditions effective to permit said phospholipase to cleave said beacon; and detecting the fluorescence of said NIR fluorophore as a function of time, wherein an increase or decrease in the quantity or rate of accumulation of fluorescence as compared to a control reaction identifies the compound as a modulator of the phospholipase.

In another embodiment, the present invention provides a phospholipase modulator identified by a method of identifying a modulator of a phospholipase in vivo, comprising the steps of: contacting a tissue comprising a phospholipase with a) a molecular beacon comprising a phospholipid moiety; a first fluorophore moiety covalently linked to the glycerol backbone of said phospholipid either directly or via a linker, wherein said first fluorophore moiety is a near infrared (NIR) fluorophore moiety; and a quencher moiety, wherein a change in fluorescence of said NIR fluorophore is detectable upon an enzymatic cleavage of said phospholipid beacon; and b) a candidate modulator compound under conditions effective to permit said phospholipase to cleave said beacon; and detecting the fluorescence of said NIR fluorophore as a function of time, wherein an increase or decrease in the quantity or rate of accumulation of fluorescence as compared to a control reaction identifies the compound as a modulator of the phospholipase.

In another embodiment, the present invention provides a method of monitoring tumor growth in vivo, comprising the steps of contacting a tumor cell with a composition comprising a molecular beacon comprising a phospholipid moiety; a first fluorophore moiety covalently linked to the glycerol backbone of said phospholipid either directly or via a linker, wherein said first fluorophore moiety is a near infrared (NIR) fluorophore moiety; and a quencher moiety, wherein a change in fluorescence of said NIR fluorophore is detectable upon an enzymatic cleavage of said phospholipid beacon; and detecting the fluorescence of said NIR fluorophore moiety as a function of time, wherein an increase in fluorescence as a function of time correlates with growth of the tumor.

In another embodiment, the present invention provides a method of identifying an inhibitor of tumor growth in vivo, comprising the steps of: contacting a tumor cell with a) a phospholipid-based near infrared (NIR) molecular beacon comprising a phospholipid moiety, a first fluorophore moiety covalently linked to the glycerol backbone of said phospholipid either directly or via a linker, wherein said first fluorophore moiety is an NIR fluorophore moiety; and a quencher moiety covalently linked to said phospholipid glycerol backbone either directly or via a linker, wherein a change in fluorescence of said NIR fluorophore is detectable upon an enzymatic cleavage of said phospholipid and b) a candidate inhibitor compound under conditions effective to permit a phospholipase to cleave said beacon; and detecting the fluorescence of said NIR fluorophore as a function of time, wherein a decrease in the quantity or rate of accumulation of fluorescence as compared to a control reaction identifies the compound as an inhibitor of tumor growth.

In another embodiment, the present invention provides a tumor inhibitor identified by a method of identifying an inhibitor of tumor growth in vivo, comprising the steps of: contacting a tumor cell with a phospholipid-based near infrared (NIR) molecular beacon comprising a phospholipid moiety, a first fluorophore moiety covalently linked to the glycerol backbone of said phospholipid either directly or via a linker, wherein said first fluorophore moiety is an NIR fluorophore moiety; and a quencher moiety covalently linked to said phospholipid glycerol backbone either directly or via a linker, wherein a change in fluorescence of said NIR fluorophore is detectable upon an enzymatic cleavage of said phospholipid and a candidate inhibitor compound under conditions effective to permit a phospholipase to cleave said beacon; and detecting the fluorescence of said NIR fluorophore as a function of time, wherein a decrease in the quantity or rate of accumulation of fluorescence as compared to a control reaction identifies the compound as an inhibitor of tumor growth.

In another embodiment, the present invention further provides a method of monitoring chronic or acute inflammation in a subject in vivo comprising the step of contacting an immune cell or inflammatory exudate with a composition comprising a molecular beacon comprising a phospholipid, a first fluorophore moiety covalently linked to the glycerol backbone of said phospholipid either directly or via a linker, wherein said first fluorophore moiety is a near infrared (NIR) fluorophore moiety; and a quencher moiety, wherein a change in fluorescence of said NIR fluorophore is detectable upon an enzymatic cleavage of said phospholipid beacon; and detecting the fluorescence of said NIR fluorophore moiety as a function of time, wherein an increase in fluorescence as a function of time correlates with an increase in inflammation.

In another embodiment, the present invention provides a method of identifying an inflammation inhibitor comprising the steps of: contacting an immune cell or inflammatory exudate with a) a phospholipid-based near infrared (NIR) molecular beacon comprising a phospholipid moiety, a first fluorophore moiety covalently linked to the glycerol backbone of said phospholipid either directly or via a linker, wherein said first fluorophore moiety is an NIR fluorophore moiety; and a quencher moiety covalently linked to said phospholipid glycerol backbone either directly or via a linker, wherein a change in fluorescence of said NIR fluorophore is detectable upon an enzymatic cleavage of said phospholipid and b) a candidate compound under conditions effective to permit a phospholipase to cleave said beacon; and detecting the fluorescence of said NIR fluorophore as a function of time, wherein a decrease in the quantity or rate of accumulation of fluorescence as compared to a control reaction identifies the compound as an inflammation inhibitor.

In another embodiment, the present invention provides an inflammation inhibitor identified by a method of identifying an inflammation inhibitor comprising the steps of: contacting an immune cell or inflammatory exudate with a phospholipid-based near infrared (NIR) molecular beacon comprising a phospholipid moiety, a first fluorophore moiety covalently linked to the glycerol backbone of said phospholipid either directly or via a linker, wherein said first fluorophore moiety is an NIR fluorophore moiety; and a quencher moiety covalently linked to said phospholipid glycerol backbone either directly or via a linker, wherein a change in fluorescence of said NIR fluorophore is detectable upon an enzymatic cleavage of said phospholipid and a candidate compound under conditions effective to permit a phospholipase to cleave said beacon; and detecting the fluorescence of said NIR fluorophore as a function of time, wherein a decrease in the quantity or rate of accumulation of fluorescence as compared to a control reaction identifies the compound as an inflammation inhibitor.

DETAILED DESCRIPTION OF THE INVENTION

Figure 1:
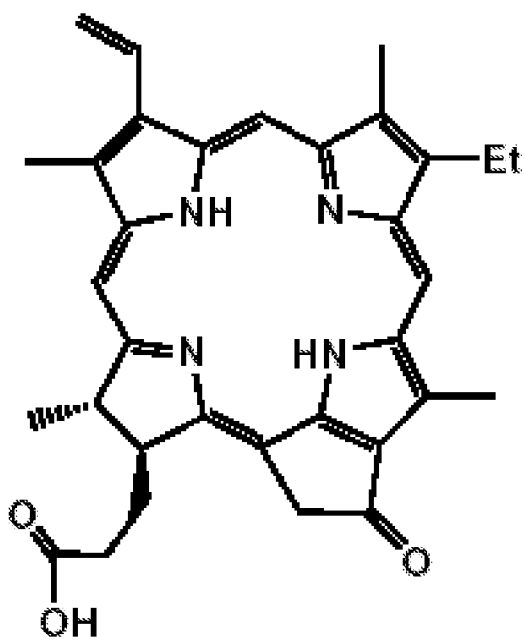
FIG. 1 shows near infrared fluorophores. Left: Pyropheophorbide a (Pyro, NIRF1) and Right: BacTeriochlorin (Bchl, NIRF2) are neutral NIR fluorophores derived from chlorophyll and bacteriochlorophyll.
Figure 1:
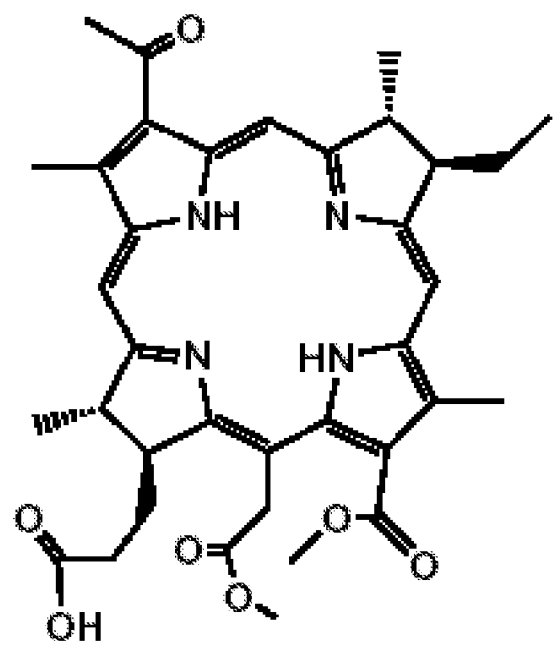

In one embodiment, provided herein is a molecular beacon, comprising a phospholipid glycerol backbone moiety; with an NIR fluorophore moiety covalently linked to a phospholipid glycerol backbone either directly or via a linker; and a quencher moiety covalently linked to a phospholipid glycerol backbone either directly or via a linker, wherein a change in fluorescence of said NIR fluorophore is detectable upon an enzymatic cleavage of said phospholipid beacon.

In another embodiment, the molecular beacons provided herein have the following general formula:

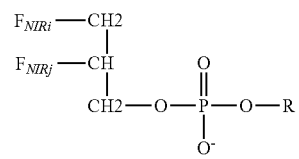

where $F_{NIRi,j}$ are the first and second NIR fluorophore or quencher and R is choline, serine, inositol or ethanolamine Each permutation representing a separate and discrete embodiment of the molecular beacons described hereinbelow and used in the methods provided herein.

In another embodiment, provided herein is a phospholipid-based near infrared (NIR) molecular beacon comprising a phospholipid moiety, a first fluorophore moiety covalently linked to the glycerol backbone of said phospholipid either directly or via a linker, wherein said first fluorophore moiety is an NIR fluorophore moiety; and a quencher moiety, wherein a change in fluorescence of said NIR fluorophore is detectable upon an enzymatic cleavage of said phospholipid. In one embodiment, said quencher moiety is covalently linked to said phospholipid glycerol backbone either directly or via a linker.

In one embodiment, the phospholipid provided herein, which is used in the molecular beacons of the methods described herein is any one of various phosphorus-containing lipids. In one embodiment, the phospholipid described herein for use in the beacons provided is lecithin, or cephalin in another embodiment. In one embodiment, the phospholipid used in the methods and compositions described comprises a glycerol backbone, a sphingosine in another embodiment. In one embodiment, the phospholipid is a phosphoglyceride (or glycerophospholipids). In one embodiment, the phospholipid is a phosphatidylcholine (PtdCho), or a phosphatidylethanolamine (PtdEtn), or a phosphatidylserine (PtdSer), or a phosphatidylinositol (PtdIns) in another embodiment. In one embodiment, the phospholipid is a phosphatidylglycerol (PtdGro). In one embodiment, the phospholipid is a cardiolipin. In one embodiment, the phospholipid is a 1-alkyl-2-acetyl-glycero-3-phosphocholine.

In one embodiment, the molecular beacon in the compositions and methods of the present invention comprises a phospholipid-glycerol backbone. In another embodiment, the molecular beacon in the compositions and methods of the present invention comprises a phospholipid moiety.

In another embodiment, the near-infrared (NIR) chromophores of the present invention absorb between 0.65-1.4 μm in wavelength.

In another embodiment, the molecular beacon described herein indicates the presence of specific phospholipid based molecules, which, in another embodiment, comprises an internally quenched fluorophore whose fluorescence is restored when it binds to a target molecule.

In another embodiment, the molecular beacon described herein is a fluorescent/quenched pair for PLC detection. In another embodiment, the fluorescent/quenched pair for PLC detection is (Pyro-PL and Pyro-PL-BHQ). In one embodiment, a similar pair for detection of PLA2 (Pyro-C12-PL and Pyro-C12-PL-BHQ), and a dual Pyro probe for PLA2 (Pyro-PyroPL) are employed for use in the invention, each in its own discrete embodiment. In another embodiment, Pyro-C12-PL-BHQ imparts an increased specificity to PLA2 relative to other phospholipase types. In another embodiment, Pyro-C12-PL-BHQ is specific to sPLA2 1B.

In another embodiment, the first NIR fluorophore used in the molecular beacons described herein and in the methods described herein, is covalently bound to a glycerol phosphate backbone either at the sn-1 fatty acyl position, the sn-2 fatty acyl position or to a glycerol phosphate backbone at sn-3 position head group in other embodiments of the present molecular beacons.

In another embodiment, the enzymatic activity which affects the changes in the fluorescence emission due to the cleavage of the phospholipid analogs described herein is performed by a phospholipase. In another embodiment, the phospholipase is phospholipase A1 which cleaves the sn-1 acyl chain. In another embodiment, the phospholipase is phospholipase A2 which cleaves the sn-2 acyl chain. In another embodiment, the phospholipase is a lysophospholipase which cleaves sn-1 acyl chain. In another embodiment, the phospholipase is phospholipase B which cleaves both sn-1 and sn-2 acyl chains. In another embodiment, the phospholipase is phospholipase C which cleaves before the phosphate, releasing diacylglycerol and a phosphate-containing head group. In another embodiment, the phospholipase is phospholipase D which cleaves after the phosphate, releasing phosphatidic acid and an alcohol.

In another embodiment, the phospholipids phosphatidylcholine, phosphatidylethanolamine and phosphatidylinositol are abbreviated as PtdCho, PtdEtn and PtdIns. In another embodiment, the soluble phospholipid metabolites, phosphocholine, phosphoethanolamine, glycerophosphocholine and glycerophosphoethanolamine are abbreviated PCho, PEtn, GPC, and GPE. In another embodiment, the phospholipase C is abbreviated PC-PLC and PtdIns-specific phospholipase C is abbreviated PI-PLC.

In another embodiment, phospholipase A2 (PLA2) removes fatty acid chains from the sn-1 and sn-2 positions of the glycerol backbone of a variety of phospholipids. In another embodiment, PLC specifically hydrolyzes the P—O bond adjacent to the glycerol sn-3 position to produce diacylglycerol and the corresponding phosphorylated head group. In another embodiment, the PLD hydrolyzes the O—P bond adjacent to the head group, releasing the head group and a molecule of phosphatidic acid. In another embodiment, phospholipases are ubiquitous enzymes in plants and animals, and perform a number of critical regulatory functions, such as signal transduction for the maintenance and turnover of membranes in one embodiment, or as mediators of inflammation and immunity and as digestive enzymes both at the cellular (i.e. lysosomal) level as well as being crucial to the absorption of nutrients through the gut in other embodiments.

In another embodiment, phospholipase A2 catalyzes the hydrolysis of the sn-2 bond of a phospholipid, creating a lysophospholipid and releasing a fatty acyl chain. In another embodiment, the phospholipase A2 is critical in a number of functions at the cellular and tissue level as a modulator of inflammation, as an important regulator of immune function, as a controlling factor in signal transduction and in membrane remodeling. In another embodiment, the PLA2 levels are increased during inflammatory response and in hyperproliferation and apoptosis. Thus, in one embodiment, the compositions and methods of the present invention may be used to monitor inflammatory response, hyperproliferation, apoptosis, or a combination thereof. In another embodiment, the compositions and methods of the present invention may be used to identify a modulator of an inflammatory response, hyperproliferation, apoptosis, or a combination thereof. In another embodiment, the PLA2 is responsible for the release of arachidonic acid and formation of lysophospholipid.

In one embodiment, lysophospholipids are signaling molecules involved in differentiation, proliferation intercellular communication and cell invasion. In another embodiment, arachidonic acid released is a precursor to prostaglandins and leukotrienes, critical modulators in inflammation, and modulators of growth and differentiation. In one embodiment, PLA2 activity and expression is elevated in cells treated with growth factors or cytokines. In another embodiment, elevated PLA2 is also found in inflammatory exudates and in autoimmune disorders, including rheumatoid arthritis and chronic inflammation. In another embodiment, there are numerous isoforms of PLA2 that are generally divided into three categories on the basis of molecular weight and requirement for calcium. In another embodiment, low molecular weight (13-16 kDa) secretory PLA2 is $Ca^{2+}$ dependent (Types II, V and X). In another embodiment, high molecular weight $Ca^{2+}$-dependent (type IV, MW 55-100 kDa), are generally cytoplasmic and require calcium for translocation, but not for activity. In another embodiment, calcium-independent (type VI-VII) PLA2 vary in molecular weight and can be secretory or cytoplasmic. In another embodiment, type II PLA2 (sPLA2) is secreted by a number of cell types including eosinophils, mast cells and neutrophils.

In another embodiment, major types of PLC include the PtdIns-specific (PI-PLC) and PtdCho specific (PC-PLC). In one embodiment, PC-PLC is an important molecular marker for cancer. In another embodiment, PI-PLC is involved in G-protein mediated and tyrosine kinase mediated signal transduction pathways. In another embodiment, PI-PLC specifically hydrolyzes a phosphorylated form of PtdIns (PIP2) into inositol triphosphate (IP3) and diacylglycerol (DAG). In another embodiment, Both DAG and IP3 are important second messengers, DAG for the activation of protein kinase C and IP3 modulating the ras, Akt and mTOR signaling pathways. In another embodiment, there are numerous isoforms of PI-PLC.

In another embodiment, a NIR fluorophore binding position on the acyl group is enzyme-specific. In another embodiment, first NIR fluorophore binding position on the acyl group is enzyme-specific. In another embodiment, second NIR fluorophore binding position on the acyl group is enzyme-specific.

In another embodiment, the second fluorophore moiety is covalently linked to a phospholipid-glycerol backbone. In another embodiment, the second fluorophore moiety is covalently linked to a phospholipid moiety through a linker. In another embodiment, a quencher moiety is covalently linked to a phospholipid moiety. In another embodiment, a quencher moiety is covalently linked to a phospholipid through a linker. In another embodiment, a beacon comprises variable moieties as known to one of skill in the art.

In one embodiment, a "moiety" is a functional group. In another embodiment, a "moiety" is a significant segment or portion of a molecule. In one embodiment, significant segment or portion describes a segment or portion that takes part in the function of the molecule.

In another embodiment, a fluorophore is a compound that fluoresces in the near infrared (NIR) region, i.e., in the range of about 675 nm to 1100 nm. In another embodiment, a fluorophore refers to a compound that fluoresces in the near infrared (NIR) region, i.e., in the range of about 700 nm to 1100 nm. In another embodiment, a fluorophore is a compound that fluoresces in the near infrared (NIR) region, i.e., in the range of about 750 nm to 1100 nm. In another embodiment, a fluorophore is a compound that fluoresces in the near infrared (NIR) region, i.e., in the range of about 800 nm to 1100 nm. In another embodiment, a fluorophore is a compound that fluoresces in the near infrared (NIR) region, i.e., in the range of about 800 nm to 900 nm. In another embodiment, a fluorophore is a compound that fluoresces in the near infrared (NIR) region, i.e., in the range of about 700 nm to 800 nm. In another embodiment, a fluorophore is a compound that fluoresces in the near infrared (NIR) region, i.e., in the range of about 650 nm to 1000 nm. In another embodiment, a fluorophore is a compound that fluoresces in the near infrared (NIR) region, i.e., in the range of about 800 nm to 900 nm. In another embodiment, a fluorophore is a compound that fluoresces in the near infrared (NIR) region, i.e., in the range of about 700 nm to 1100 nm.

In another embodiment, the fluorophore used in the compositions and methods of the present invention is an organic NIR fluorophore. In another embodiment, the fluorophore is a polymethine. In another embodiment, the fluorophore is a pentamethine. In another embodiment, the fluorophore is a heptamethine cyanine. In another embodiment, the fluorophore comprises benzoxazole. In another embodiment, the fluorophore comprises benzothaizole. In another embodiment, the fluorophore comprises indolyl, 2-quinoline. In another embodiment, the fluorophore comprises 4-quinoline. In another embodiment, the fluorophore is a pyropheophorbide. In another embodiment, the fluorophore is a pyropheophorbol. In another embodiment, the fluorophore is a bacteriochlorophyll. In another embodiment, the fluorophore is derived from a chlorophyll and bacteriochlorophyll. In another embodiment, the fluorophore is a pyropheophorbide and bacteriochlorin. In another embodiment, the fluorophore is bacteriochlorin. In another embodiment, the fluorophore is pyropheophorbide a. In another embodiment, the fluorophore is a Cy5.5. In one embodiment, any of the fluorophores described herein may be used as the first fluorophore or as the second fluorophore.

In another embodiment, the quencher moiety used in the beacons described herein, which are used in the methods provided herein, is a second fluorophore or a dark quencher, in another embodiment. In one embodiment, the quencher moiety is covalently bound to the remaining unbound fatty acyl position. In another embodiment, the quencher moiety is covalently bound to glycerol phosphate backbone either at the sn-1 fatty acyl position, the sn-2 fatty acyl position or to a glycerol phosphate backbone at sn-3 position head group.

In another embodiment, a quencher of the compositions and methods of the present invention is a black hole quencher 3 (BHQ3). In another embodiment, the quencher is BHQ. In another embodiment, the quencher is BlackBerrry Quencher 650. In another embodiment, the quencher is $^1O_2$ quencher. In another embodiment, the quencher is BHQ-1 534, BHQ-2 580, BHQ-3 670 (in one embodiment, Black Hole quenchers (BHQ) are available from Biosearch Technologies), Dabcyl 475, DDQ-I 430, DDQ-II A 630 (in one embodiment, Deep Dark Quenchers (DDQ) are available from Eurogentec), Eclipse 530, which in one embodiment, is available from Epoch Biosciences, Iowa Black FQ 532, Iowa Black RQ 645 (in one embodiment, Iowa quenchers are available from Integrated DNA Technologies), QSY-21 660, or QSY-7 571 (in one embodiment, QSY quenchers are available from Molecular Probes). In another embodiment, the quencher is a derivative of 3- and/or 6-amino xanthenes. In another embodiment, the quencher is a non-fluorescent cyanine type dyes. In another embodiment, the quencher is a nitro-substituted non-fluorescent asymmetric cyanine dye compound.

In one embodiment, BHQ acts as an effective quencher of Pyro fluorescence, reducing the fluorescence emission relative to Pyro-PL between 25-fold and 45-fold. In another embodiment, BHQ reduces the fluorescence emission relative to Pyro-PL between 25-fold and 40-fold. In another embodiment, the reduction of fluorescence emission is between 30-fold and 40-fold. In yet another embodiment, the reduction in fluorenscence emission is between 35-fold and 45-fold.

In one embodiment, fluorescein is used as the reporter and rhodamine as the quencher (FAM/TAM probes). In one embodiment, the mechanism by which energy can be transferred nonradiatively (without absorption or emission of photons) between two dyes, a donor and an acceptor dye is Förster resonance energy transfer (FRET or FET), Dexter (also known as exchange or collisional energy transfer) or static quenching (also referred to as contact quenching). Dyes that work via these distinct mechanisms are known in the art and are considered an embodiment of the invention.

In one embodiment, a "quencher" is a substance that absorbs excitation energy from a fluorophore. In one embodiment, a typical fluorescent quencher re-emits much of this energy as light. In one embodiment, a "dark quencher" dissipates the absorbed energy as heat. In one embodiment, dark quenchers are used in molecular biology in conjunction with fluorophores where, in one embodiment, when they are close together, the fluorophore's emission is suppressed.

In another embodiment, a fluorophore is visualized by a low-light camera and appropriate filters that collect emission light from the specimen. In another embodiment, a camera is connected to magnification means. In another embodiment, camera is connected to a microscope. In another embodiment, camera is connected to a confocal microscope. In another embodiment, camera is further connected to a computer. In another embodiment, computer stores images obtained from the camera.

In another embodiment, provided herein is a method of analyzing a sample for the presence of a phospholipase. In one embodiment, the method comprises contacting a sample suspected of containing a phospholipase with a phospholipid-based NIR molecular beacon, comprising a phospholipid moiety; a first NIR fluorophore moiety covalently linked to the phospholipid moiety either directly or via a linker; and a quencher moiety, wherein a change in fluorescence of said NIR fluorophore is detectable upon an enzymatic cleavage of said phospholipid beacon; and detecting the fluorescence of said NIR fluorophore moiety as a function of time, wherein an increase in fluorescence as a function of time correlates with the presence of the phospholipase in the sample. In one embodiment, the increase of fluorescent signal observed over the background signal is in the order of 150-fold. In one embodiment, the increase of fluorescent signal observed over the background signal is in the order of 1000-fold.

In another embodiment, the methods described herein for using the molecular beacons provided, are used to detect the presence and activity of phospholipases, which may be PLA1, PLA2, PLB, PLC, PLD or lysosphospholipase in a cell. In another embodiment, the phospholipases are PC-PLC, phosphatidylinositol-specific PLC (PI-PLC), sphingomyelinase (SMase), PC-specific PLD (PC-PLD), type IA secretory phospholipase A2 (sPLA2) and type IB sPLA2, each in its own discrete embodiment. In other embodiments, it is to be understood by a skilled artisan that the molecular beacons provided herein are specific to other isoforms of PLA2 and PLC available in the art.

Cell, as used herein does not refer to a whole human being, but rather to cells in the human being or a mammal in certain embodiments. In one embodiment, the cell in which phospholipase activity is sought to be detected refers to any cell in which such activity can be found, regardless of its origin, function, immortality or size. In another embodiment, a sample comprises a tumor cell. In another embodiment, a sample comprises an extract of a tumor cell. In another embodiment, cell of the present invention is a prokaryotic or eukaryotic cell.

In another embodiment, the cell is derived from a cell line. In another embodiment, the cell is derived from a cancerous cell line. In another embodiment, the cell is derived from an immortalized cell line. In another embodiment, the cell is derived from a primary cell culture. In another embodiment, primary cell culture is derived from a tumor or cell metastasis.

In one embodiment, a beacon as described herein is a signaling or guiding device, which in one embodiment, is an indicator of the presence of a phospholipase in a sample. In one embodiment, the beacons described hereinabove are used in the methods described herein.

Accordingly and in another embodiment, provided herein is a method of identifying the activity of a phospholipase in vivo, comprising the steps of: exposing a tissue containing a phospholipase to the molecular beacon described herein, under conditions effective to permit the phospholipase to cleave a phospholipid glycerol backbone; and detecting the fluorescence emitted by the fluorescent moiety. In another embodiment, provided herein is a method of identifying the activity of a phospholipase in vivo, comprising the steps of: exposing a tissue containing a phospholipase to a molecular beacon under conditions effective to permit the phospholipase to cleave a beacon; and detecting the fluorescence emitted by the fluorescent moiety as a function of time, wherein an increase in the quantity or rate of accumulation of fluorescence as compared to a control reaction identifies the presence of the phospholipase.

In another embodiment, the present invention provides a method of monitoring the activity of a phospholipase in vivo, comprising the steps of: exposing a tissue to a molecular beacon comprising a phospholipid moiety; a first fluorophore moiety covalently linked to the glycerol backbone of said phospholipid either directly or via a linker, wherein said first fluorophore moiety is a near infrared (NIR) fluorophore moiety; and a quencher moiety, wherein a change in fluorescence of said NIR fluorophore is detectable upon an enzymatic cleavage of said phospholipid beacon; and detecting the fluorescence of said fluorophore moiety as a function of time, wherein an increase in the quantity or rate of accumulation of fluorescence as compared to a control reaction identifies the activity of the phospholipase.

In another embodiment, the molecular beacons include longer wavelength fluorophores in order to reduce background fluorescence. In another embodiment, the molecular beacons are used to design specific phospholipase resistant probes to be used as controls. In another embodiment, specific phospholipase resistant probes may be implemented in sophisticated mouse models of human cancer.

In another embodiment, provided herein is a method of identifying a modulator of a phospholipase. In another embodiment, provided herein is a method of identifying a modulator of a phospholipase in vivo. In another embodiment, provided herein is a method of identifying a modulator of a phospholipase in vitro. In another embodiment, provided herein is a method of identifying a modulator of a phospholipase, comprising the steps of: contacting a phospholipase with a molecular beacon as described herein and a candidate modulator compound under conditions effective to permit the phospholipase to cleave the beacon; and detecting the fluorescence of the fluorescent moiety. In another embodiment, provided herein is a method of identifying a modulator of a phospholipase, comprising the steps of: contacting a phospholipase, with a molecular beacon as described herein and a candidate modulator compound under conditions effective to permit the phospholipase to cleave the beacon; and detecting the fluorescence of said NIR fluorophore moiety as a function of time. In another embodiment, provided herein is a method of identifying a modulator of a phospholipase comprising the steps of: contacting a phospholipase with a molecular beacon as described herein and a candidate modulator compound under conditions effective to permit the phospholipase to cleave the beacon; and detecting the fluorescence of said NIR fluorophore moiety as a function of time, wherein an increase or decrease in the quantity or rate of accumulation of fluorescence as compared to a control reaction identifies the compound as a modulator of the phospholipase. In another embodiment, modulator is an enhancer. In another embodiment, modulator is an inhibitor.

In another embodiment, provided herein is a modulator of a phospholipase, detected by the methods described herein. In another embodiment, a modulator of phospholipase is a phospholipase enhancer. In another embodiment, a modulator of phospholipase is a phospholipase inhibitor. In another embodiment, the present invention provides a phospholipase modulator identified by a method of identifying a modulator of a phospholipase in vivo, comprising the steps of: contacting a tissue comprising a phospholipase with a) a molecular beacon comprising a phospholipid moiety; a first fluorophore moiety covalently linked to the glycerol backbone of said phospholipid either directly or via a linker, wherein said first fluorophore moiety is a near infrared (NIR) fluorophore moiety; and a quencher moiety, wherein a change in fluorescence of said NIR fluorophore is detectable upon an enzymatic cleavage of said phospholipid beacon; and b) a candidate modulator compound under conditions effective to permit said phospholipase to cleave said beacon; and detecting the fluorescence of said NIR fluorophore as a function of time, wherein an increase or decrease in the quantity or rate of accumulation of fluorescence as compared to a control reaction identifies the compound as a modulator of the phospholipase.

In one embodiment, conditions effective to permit said phospholipase to cleave said beacon are described herein in the examples section and are known in the art. Similarly, methods for determining such conditions are known in the art and described herein.

In another embodiment, provided herein is a method of monitoring cancer cell proliferation comprising the step of contacting a cancer cell with a composition comprising a molecular beacon comprising a phospholipid moiety; a first NIR fluorophore moiety covalently linked to the phospholipid moiety either directly or via a linker; and a quencher moiety, whereupon an enzyme cleavage of the phospholipid, change in fluorescence of the first fluorophore is detectable; and detecting the fluorescence of the NIR fluorescent moiety as a function of time, wherein an increase in fluorescence as a function of time correlates with proliferation of the a cancer cell.

In another embodiment, provided herein is a method of monitoring cancer cell proliferation. In another embodiment, provided herein is a method of monitoring cancer cell proliferation in vitro. In another embodiment, provided herein is a method of monitoring cancer cell proliferation in vivo. In another embodiment, provided herein is a method of monitoring tumor growth in vivo. In another embodiment, provided herein is a method of monitoring tumor growth. In another embodiment, provided herein is a method of monitoring cell metastasis.

In one embodiment, the compositions and methods of the present invention are for monitoring tumor growth or identifying an inhibitor of tumor growth. In one embodiment, the tumor is a solid tumor. In one embodiment, the tumor is a melanoma. In another embodiment, the tumor is a sarcoma. In another embodiment, the tumor is a carcinoma. In another embodiment, the tumor is a mesothelioma (e.g. malignant mesothelioma). In another embodiment, the tumor is a glioma. In another embodiment, the tumor is a germ cell tumor. In another embodiment, the tumor is a choriocarcinoma.

In one embodiment, the compositions and methods of the present invention are for monitoring cancer growth in vivo or identifying an inhibitor of cancer growth. In one embodiment, the cancer is pancreatic cancer. In another embodiment, the cancer is ovarian cancer. In another embodiment, the cancer is gastric cancer. In another embodiment, the cancer is a carcinomatous lesion of the pancreas. In another embodiment, the cancer is pulmonary adenocarcinoma. In another embodiment, the cancer is colorectal adenocarcinoma. In another embodiment, the cancer is pulmonary squamous adenocarcinoma. In another embodiment, the cancer is gastric adenocarcinoma. In another embodiment, the cancer is an ovarian surface epithelial neoplasm (e.g. a benign, proliferative or malignant variety thereof). In another embodiment, the cancer is an oral squamous cell carcinoma. In another embodiment, the cancer is non smallcell lung carcinoma. In another embodiment, the cancer is an endometrial carcinoma. In another embodiment, the cancer is a bladder cancer. In another embodiment, the cancer is a head and neck cancer. In another embodiment, the cancer is a prostate carcinoma.

In another embodiment, the cancer is a non-small cell lung cancer (NSCLC). In another embodiment, the cancer is a Wilms' tumor. In another embodiment, the cancer is a desmoplastic small round cell tumor. In another embodiment, the cancer is a colon cancer. In another embodiment, the cancer is a lung cancer. In another embodiment, the cancer is an ovarian cancer. In another embodiment, the cancer is a uterine cancer. In another embodiment, the cancer is a thyroid cancer. In another embodiment, the cancer is a hepatocellular carcinoma. In another embodiment, the cancer is a thyroid cancer. In another embodiment, the cancer is a liver cancer. In another embodiment, the cancer is a renal cancer. In another embodiment, the cancer is a kaposis. In another embodiment, the cancer is a kaposis sarcoma. Each possibility represents a separate embodiment of the present invention.

In one embodiment, the compositions and methods of the present invention are for monitoring cell metastasis or identifying an inhibitor of cell metastasis. In one embodiment, metastasis is a process by which cancer spreads from the place at which it first arose as a primary tumor to distant locations in the body. In one embodiment, a cancer of the present invention is a breast cancer metastasis. In another embodiment, a cancer of the present invention is a melanoma metastasis. In one embodiment, the cancer metastasizes to the brain. In another embodiment, the cancer metastasizes to the lung. In another embodiment, the cancer metastasizes to the kidney. In another embodiment, the cancer metastasizes to the colon. In another embodiment, the cancer, which in one embodiment, is a breast cancer, metastasizes to the breast or the area where the breast used to be, the chest wall, the lymph nodes, the bones, the lungs or around the lungs, the liver, the brain, or a combination thereof. In another embodiment, the cancer, which in one embodiment, is a melanoma, metastasizes to skin (other areas of the skin), subcutaneous tissue and lymph nodes, lungs and area between the lungs, liver, brain, bone, gastrointestinal tract, heart, pancreas, adrenal glands, kidneys, thyroid, or a combination thereof.

In one embodiment, this invention provides compositions and methods for monitoring cancer, tumors, metastasis, or a combination thereof in populations that are predisposed to the cancer or in populations that are at high risk for the cancer, which in one embodiment, may be a population of women with brca1 or brca2 mutations, which population in one embodiment is susceptible to breast cancer.

In another embodiment, provided herein is a method of identifying an inhibitor of cell proliferation comprising the steps of: contacting a cell, with a molecular beacon and a candidate inhibitor compound under conditions effective to permit a phospholipase to cleave the beacon; and detecting the fluorescence of the NIR fluorescent moiety as a function of time, wherein a decrease in the quantity or rate of accumulation of fluorescence as compared to a control reaction identifies the compound as an inhibitor of tumor growth. In another embodiment, provided herein is a method of identifying an inhibitor of cell proliferation. In another embodiment, provided herein is a method of identifying an inhibitor of cell proliferation in vivo. In another embodiment, provided herein is a method of identifying an inhibitor of cell proliferation in vitro. In another embodiment, provided herein is a method of identifying an inhibitor of growth in vivo, comprising the steps of: contacting a cell, with a molecular beacon and a candidate inhibitor compound under conditions effective to permit a phospholipase to cleave the beacon of claim 1; and detecting the fluorescence of the NIR fluorescent moiety as a function of time, wherein a decrease in the quantity or rate of accumulation of fluorescence as compared to a control reaction identifies the compound as an inhibitor of growth.

In another embodiment, the present invention provides a method of monitoring tumor growth in vivo, comprising the steps of contacting a tumor cell with a composition comprising a molecular beacon comprising a phospholipid moiety; a first fluorophore moiety covalently linked to the glycerol backbone of said phospholipid either directly or via a linker, wherein said first fluorophore moiety is a near infrared (NIR) fluorophore moiety; and a quencher moiety, wherein a change in fluorescence of said NIR fluorophore is detectable upon an enzymatic cleavage of said phospholipid beacon; and detecting the fluorescence of said NIR fluorophore moiety as a function of time, wherein an increase in fluorescence as a function of time correlates with growth of the tumor.

In another embodiment, the present invention provides a method of identifying an inhibitor of tumor growth in vivo, comprising the steps of: contacting a tumor cell with a) a phospholipid-based near infrared (NIR) molecular beacon comprising a phospholipid moiety, a first fluorophore moiety covalently linked to the glycerol backbone of said phospholipid either directly or via a linker, wherein said first fluorophore moiety is an NIR fluorophore moiety; and a quencher moiety covalently linked to said phospholipid glycerol backbone either directly or via a linker, wherein a change in fluorescence of said NIR fluorophore is detectable upon an enzymatic cleavage of said phospholipid and b) a candidate inhibitor compound under conditions effective to permit a phospholipase to cleave said beacon; and detecting the fluorescence of said NIR fluorophore as a function of time, wherein a decrease in the quantity or rate of accumulation of fluorescence as compared to a control reaction identifies the compound as an inhibitor of tumor growth.

In another embodiment, the present invention provides a tumor inhibitor identified by a method of identifying an inhibitor of tumor growth in vivo, comprising the steps of: contacting a tumor cell with a phospholipid-based near infrared (NIR) molecular beacon comprising a phospholipid moiety, a first fluorophore moiety covalently linked to the glycerol backbone of said phospholipid either directly or via a linker, wherein said first fluorophore moiety is an NIR fluorophore moiety; and a quencher moiety covalently linked to said phospholipid glycerol backbone either directly or via a linker, wherein a change in fluorescence of said NIR fluorophore is detectable upon an enzymatic cleavage of said phospholipid and a candidate inhibitor compound under conditions effective to permit a phospholipase to cleave said beacon; and detecting the fluorescence of said NIR fluorophore as a function of time, wherein a decrease in the quantity or rate of accumulation of fluorescence as compared to a control reaction identifies the compound as an inhibitor of tumor growth.

In another embodiment, provided herein is a method of monitoring acute inflammation in a subject in vivo, comprising the step of contacting an immune cell or inflammatory exudate with a composition comprising a molecular beacon comprising a phospholipid, a first fluorophore moiety covalently linked to the glycerol backbone of said phospholipid either directly or via a linker, wherein said first fluorophore moiety is a near infrared (NIR) fluorophore moiety; and a quencher moiety, wherein a change in fluorescence of said NIR fluorophore is detectable upon an enzymatic cleavage of said phospholipid beacon; and detecting the fluorescence of said NIR fluorophore moiety as a function of time, wherein an increase in fluorescence as a function of time correlates with an increase in inflammation.

In one embodiment, an "exudate" is a fluid rich in protein and cellular elements that oozes out of blood vessels due to inflammation and is deposited in nearby tissues. In one embodiment, the altered permeability of blood vessels as a result of inflammation permits the passage of large molecules and solid matter, such as those found in exudate, through the blood vessel wall.

In another embodiment, provided herein is a method of monitoring chronic inflammation in a subject in vivo, comprising the step of contacting an immune cell or inflammatory exudate with a composition comprising a molecular beacon comprising a phospholipid, a first fluorophore moiety covalently linked to the glycerol backbone of said phospholipid either directly or via a linker, wherein said first fluorophore moiety is a near infrared (NIR) fluorophore moiety; and a quencher moiety, wherein a change in fluorescence of said NIR fluorophore is detectable upon an enzymatic cleavage of said phospholipid beacon; and detecting the fluorescence of said NIR fluorophore moiety as a function of time, wherein an increase in fluorescence as a function of time correlates with an increase in inflammation.

In another embodiment, provided herein is a method of monitoring chronic or acute inflammation in a subject in vivo, comprising the step of contacting an immune cell or inflammatory exudate with a composition comprising a molecular beacon comprising a phospholipid, a first fluorophore moiety covalently linked to the glycerol backbone of said phospholipid either directly or via a linker, wherein said first fluorophore moiety is a near infrared (NIR) fluorophore moiety; and a quencher moiety, wherein a change in fluorescence of said NIR fluorophore is detectable upon an enzymatic cleavage of said phospholipid beacon; and detecting the fluorescence of said NIR fluorophore moiety as a function of time, wherein an increase in fluorescence as a function of time correlates with an increase in inflammation.

In another embodiment, provided herein is a method of monitoring chronic or acute inflammation in vitro, comprising the step of contacting an immune cell or inflammatory exudate with a composition comprising a molecular beacon comprising a phospholipid, a first fluorophore moiety covalently linked to the glycerol backbone of said phospholipid either directly or via a linker, wherein said first fluorophore moiety is a near infrared (NIR) fluorophore moiety; and a quencher moiety, wherein a change in fluorescence of said NIR fluorophore is detectable upon an enzymatic cleavage of said phospholipid beacon; and detecting the fluorescence of said NIR fluorophore moiety as a function of time, wherein an increase in fluorescence as a function of time correlates with an increase in inflammation.

In another embodiment, provided herein is a method of identifying an inflammation inhibitor, comprising the steps of: contacting an inflammatory exudate, with a molecular beacon as described herein and a candidate compound under conditions effective to permit a phospholipase to cleave the beacon; and detecting the fluorescence of the NIR fluorescent moiety, wherein a decrease in the quantity or rate of accumulation of fluorescence as compared to a control reaction identifies the compound as an inflammation inhibitor. In another embodiment, provided herein is a method of identifying an inflammation inhibitor, comprising the steps of contacting an immune cell with a molecular beacon as described herein and a candidate compound under conditions effective to permit a phospholipase to cleave the beacon; and detecting the fluorescence of the NIR fluorescent moiety, wherein a decrease in the quantity or rate of accumulation of fluorescence as compared to a control reaction identifies the compound as an inflammation inhibitor.

In another embodiment, provided herein is a method of identifying an inflammation inhibitor, comprising the steps of contacting an immune cell or inflammatory exudate, with a molecular beacon as described herein and a candidate compound under conditions effective to permit a phospholipase to cleave the beacon; and detecting the fluorescence of the NIR fluorescent moiety as a function of time, wherein a decrease in the quantity or rate of accumulation of fluorescence as compared to a control reaction identifies the compound as an inflammation inhibitor.

In another embodiment, provided herein is an inflammatory mediator identified by the methods of the present invention. In another embodiment, provided herein is an inflammatory inhibitor identified by the methods of the present invention. In another embodiment, provided herein is an inflammatory inducer identified by the methods of the present invention.

In another embodiment, provided herein is a method of modeling fluorophore activation in vivo.

In one embodiment, compositions of the present invention may comprise a NIR molecular beacon, while in another embodiment, they may consist essentially of a NIR molecular beacon, while in another embodiment, they may consist of a NIR molecular beacon. In one embodiment, molecular beacons of the present invention may comprise a phospholipid moiety, consist essentially of a phospholipid moiety, or consist of a phospholipid moiety. Similarly, methods of the present invention may comprise the steps described, consist essentially of the steps described, or consist of the steps described.

In some embodiments, the term "comprise" refers to the inclusion of the indicated active agent, such as a phospholipid moiety as described herein, or method step, as well as inclusion of other active agents, and pharmaceutically acceptable carriers, excipients, emollients, stabilizers, etc., as are known in the pharmaceutical industry. In some embodiments, the term "consisting essentially of" refers to a composition, whose only active ingredient is the indicated active ingredient, however, other compounds may be included which are for stabilizing, preserving, etc. the formulation, but are not involved directly in the diagnostic or therapeutic effect of the indicated active ingredient. Similarly, a method consisting essentially of a particular step may include other steps, but not steps that significantly affect the diagnostic or therapeutic result of the process. In some embodiments, the term "consisting essentially of" may refer to components which facilitate the release of the active ingredient. In some embodiments, the term "consisting" refers to a composition, which contains the active ingredient and a pharmaceutically acceptable carrier or excipient, or, alternatively, a method that uses only the step or steps described.

The following examples are presented in order to more fully illustrate the preferred embodiments of the invention. They should in no way be construed, however, as limiting the broad scope of the invention.

EXPERIMENTAL DETAILS

Reagents and Methods

Pyro-PL-BHQ Synthesis

Five prototype phospholipid-based molecular beacons have been synthesized, a fluorescent/quenched pair for PLC detection (Pyro-PL and Pyro-PL-BHQ), a similar pair for detection of PLA2 (Pyro-C12-PL and Pyro-C12-PL-BHQ), and a dual Pyro probe for PLA2 (PyroPyroPL). Pyro-PL and Pyro-PL-BHQ, were synthesized by substituting Pyro onto the sn-2 position of the glycerol backbone in place of the fatty acid normally present. This was performed by acylating N-Boc 1-palmitoyl-sn-glycero-3-lyso-PtdEtn (Lyso-PE-NBoc) with Pyro acid after Boc-deprotection to give the permanently fluorescent analog (Pyro-PL). A second N-acylation of Pyro-PL with BHQ gave rise to the desired probe, Pyro-PL-BHQ. The third and fourth probes, Pyro-C12-PL and Pyro-C12-PL-BHQ are analogs of the two prototype probes, but containing a C12 spacer between the fluorescent Pyro moiety and the sn-2 position of the glycerol backbone. Pyro-C12-PL-BHQ was synthesized by inserting a omega-aminolauric acid spacer ($NH_2(CH_2)_{11}CO_2H$) between the Pyro fluorophore and the sn-2 position on the glycerol backbone. The fifth probe, PyroPyro-PL, was synthesized by directly acetylating two Pyro moieties, containing C6 spacers, onto the glycerol sn-1 and sn-2 positions of sn-glycero-3-phosphocholine. Three of these molecular beacons, Pyro-PL-BHQ, Pyro-C12-PL-BHQ and PyroPyro-PL, are self-quenching. In Pyro-PL-BHQ and Pyro-C12-PL-BHQ, the Pyro is quenched by BHQ3; in PyroPyro-PL, by intramolecular interactions between the two Pyro moieties. Moreover these three probes are potentially enzyme activated—the first two by either PLA2, PLC or PLD, the third by PLA2 only. The Cm spacers were inserted of between Pyro fluorophore and glycerol backbone to modulate the enzyme specificity of these probes. The Pyro-PL and Pyro-C12-PL are permanently fluorescent, and are important for calibrating in vitro assays and for performing in vivo bio-distribution studies.

Figure 2:
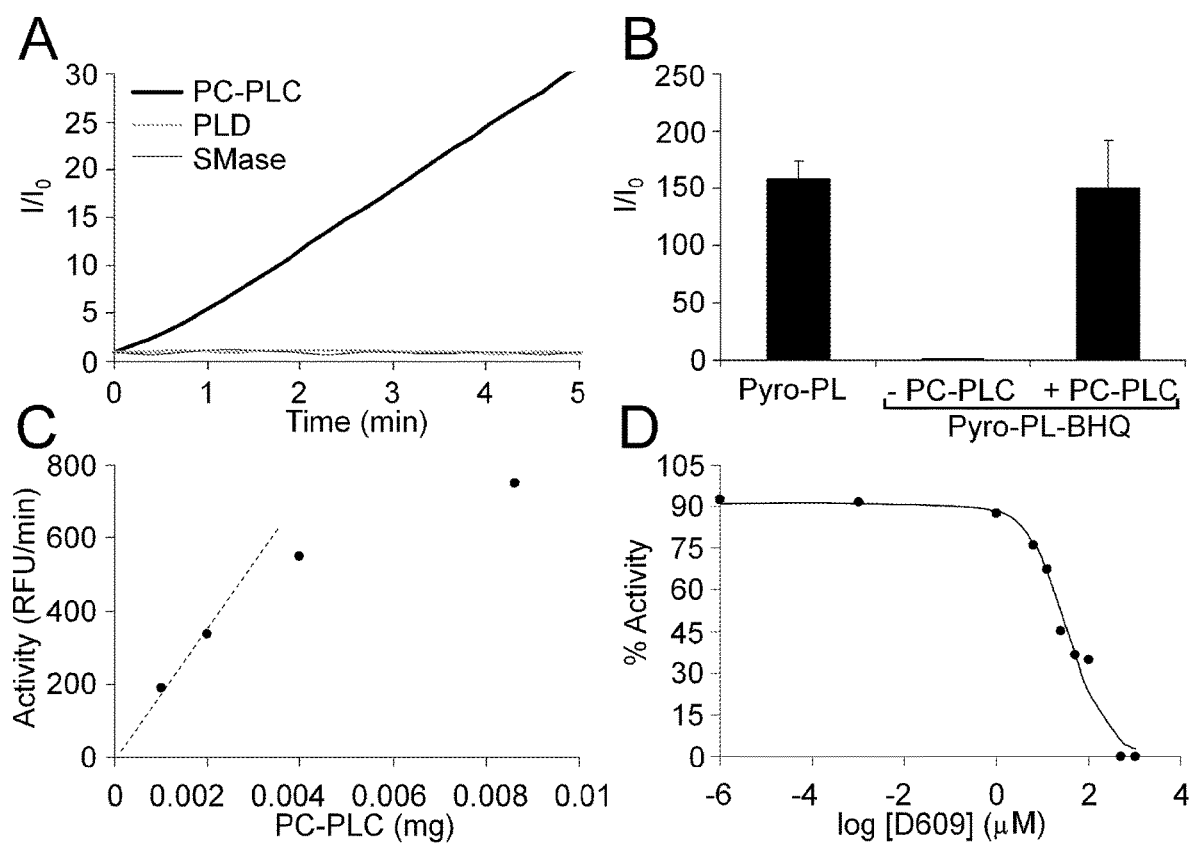
FIG. 2 shows the characterization of Pyro-PL-BHQ. (A) Time-dependent increase in fluorescence of 1 µM Pyro-PL-BHQ incubated with 10 U each of PC-PLC, PLD or SMase; (B) fold increase in fluorescence (665 nm) of 1 µM Pyro-PL-BHQ before and after complete activation by PC-PLC, as compared to that of Pyro-PL at equal concentrations (error bars represent s.d., n=3); (C) dependence of fluorescence release from Pyro-PL-BHQ on PC-PLC concentration; (D) Inhibition of PC-PLC activity toward 1 µM Pyro-PL-BHQ by D609 ($IC_{50}$ of 34±8 µM).

In further detail, Pyro-PL-BHQ was synthesized from 1-palmitoyl lysophosphatidylethanolamine by first attaching pyropheophorbide a ($\lambda_{ex}$ 418, 675 nm; $\lambda_{em}$ 670-730 nm) to the sn-2 position on the glycerol backbone. The head group was then conjugated to the Black Hole Quencher 3 (BHQ3), which absorbs strongly from 650-700 nm. This probe is naturally self-quenching until enzymatically cleaved, separating pyropheophorbide from BHQ3. Pyro-PL-BHQ was dispersed in liposomes of phosphatidylcholine and incubated at 37° C. with 1 unit of various phospholipases: PC-PLC, phosphatidylinositol-specific PLC (PI-PLC), sphingomyelinase (SMase), PC-specific PLD (PC-PLD), type IA secretory phospholipase A2 (sPLA2) and type IB sPLA2. Relative affinities of these enzymes to Pyro-PL-BHQ were determined by measuring the time-dependent release of fluorescence on a fluorescent plate reader ($\lambda$ex 418 nm; $\lambda$em 675 nm) (FIG. 2A). A full kinetic analysis (Vmax, Km) was performed to determine the affinity of PC-PLC for Pyro-PL-BHQ. This included measuring the effects of enzyme and substrate concentration, and correcting for surface dilution and self-quenching effects.

Figure 14:
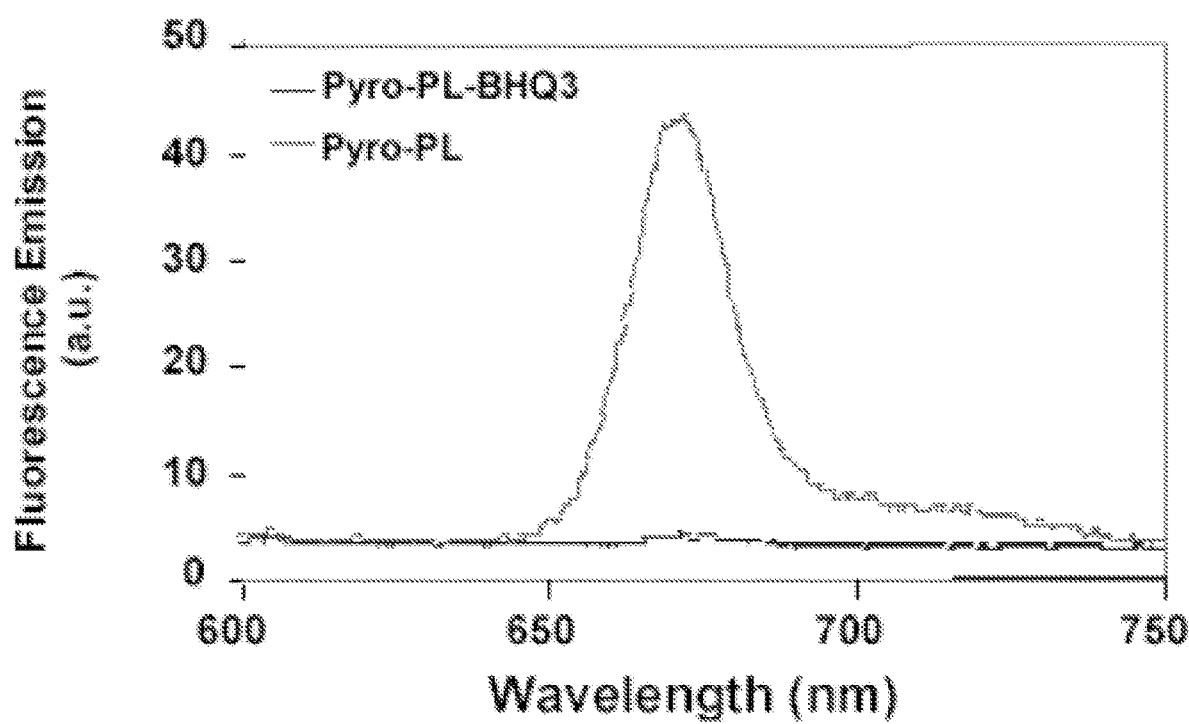
FIG. 14 shows the quenching effect of BHQ3 on Pyro. Fluorescence emission spectra show intermolecular quenching by BHQ reduces fluorescence 40 fold in Pyro-PL-BHQ compared to the un-quenched phospholipid analog Pyro-PL.

In Pyro-PL-BHQ, BHQ acts as an effective quencher of Pyro fluorescence, reducing the fluorescence emission relative to Pyro-PL between 25-fold (for $\lambda$ex=675, $\lambda$em=725 nm) and 45-fold (for $\lambda$ex=418, $\lambda$em=695 nm) (FIG. 14).

TLC Assay.

A 2 mL volume of a sonicated 200 µM Pyro-PL-BHQ/egg-PtdCho (1:20) lipid dispersion was divided into aliquots of 200 µL and each was incubated at 37° C. with 1 U of enzyme: PC-PLC, PI-PLC, SMase, PC-PLD, type IA sPLA2 or type IB sPLA2. After 24 hours, a sample from each aliquot was separated on an UV Silica Gel TLC plate using the solvent chloroform:methanol (100:15). Fluorescent bands due to cleavage were detected using an UV lamp at 385 nm and the Rf of each band was compared to a control Pyro-PL-BHQ/lipid dispersion that had not been exposed to enzyme.

Cell Culture

DU145 cells were maintained in RPMI 1640, 10% FCS, 2 mM L-glutamine, penicillin/streptomycin in 150 cm2 filter cap flasks using at 37° C. with 5% CO2 in air. For NMR studies of perfused cells, $8 \times 10^6$ cells are seeded on 2.5 ml of Biosilon microcarrier beads (NUNC, Denmark) in bacteriological petri dishes.

Human Non-Hodgkin's lymphoma line WSU-DLCL2 is maintained in MEM Eagle and RPMI 1640 culture medium respectively supplemented with 10% fetal calf serum, 2 mM L-glutamine, penicillin/streptomycin and 20 mM $NaHCO_3$. Cultures are routinely grown in 150 $cm^2$ filter cap tissue culture flasks using standard culture conditions of 37° C. and 5% $CO_2$ in air. For extracts, cells are seeded at $1 \times 10^5$ cells/mL in 150-$cm^2$ flasks and incubated for 24 h.

Tumor Xenografts in Athymic Mice

DU145 DLCL2 NHL human tumor cells were injected subcutaneously into the flanks of 4-6 wk old male athymic (nu/nu) mice (Charles River Laboratories, Wilmington, Mass.). Tumors are studied from 4-9 wks after implantation. Tumor growth are assessed by caliper volume measurements and calculated using the formula Vol.=$(\pi/6) \times a \times b \times c$, where a, b, c are three mutually orthogonal diameters.

Enzyme Assays

Fluorescence Microscopy and Flow Cytometry

DU145 cells ($10^5$ cells/ml) are seeded into Nunc chambered culture slides and incubated for 24 h. PB in culture medium (or control PBS) is added to a final concentration of 10 mM and the cells are incubated for 4-6 h. The cells are washed in PBS, and overlaid with 10 µl of 0.75 mM DPPC/fluorophore (160:1 mol ratio) vesicles in PBS and incubated for 1 h at 37° C. The cells are washed and mounted for microscopy on a Leica TCS SPII laser scanning confocal microscope. For flow cytometry, DU145 cells are seeded at $10^5$ cells/ml into 150 cm² flasks, incubated for 24 h and PB or sham-treatment performed. Harvested cells are incubated with pro-fluorophore mixed vesicles as described above and analyzed on a Becton Dickinson FACScalibur using FL4 (bandpass>670 nm).

Fluorescence Spectroscopy.

A Molecular Devices SpectraMax M5 microplate reader was used to measure the fluorescence from 100 µL volume sample-containing wells of a black 96-well plate. The excitation and emission wavelengths for detecting Pyro fluorescence were set to 410 nm and 675 nm, respectively. A 495 nm cut-off filter was selected to reduce excitation artifacts. The initial rate was determined using the SoftMax Pro Software (Molecular Devices, Sunnyvale, Calif.). An aliquot of phospholipid is placed in a cuvette in 50 mM Tris (pH 8, 100 mM NaCl, 1 mM CaCl2), equilibrated at 35° C. for several minutes and the background emission recorded. Porcine pancreatic, bacterial or human phospholipase is added (1-10 µL) and emission recorded as a function of time. To calibrate the assay, a measured amount of a standard near infrared fluorophore (NIRF) is added to the wells, and the increase in 0 recorded, and converted to a rate of product conversion (pmoles $sec^{-1}$).

Co-Registration of Imaging and Histology

Phospholipids and Phospholipases

L-α-phosphatidylcholine (PtdCho. chicken egg), L-α-phosphatidyl-DL-glycerol (PtdGro, chicken egg, sodium salt), and cholesterol are obtained from Avanti Polar Lipids, Inc. (Alabaster, Ala.), L-α-phosphatidylethanolamine (PtdEtn, chicken egg) and sphingomyelin (SM, bovine brain) are obtained from Sigma-Aldrich (St. Louis, Mo.). All phospholipids are stored as chloroform solutions at −20° C. Recombinant human sPLA2-IB, IIA, IID, IIE, V, X and XII are obtained from ProSpec-Tany TechoGene Ltd. (Rehovot, Israel). Broad spectrum (PLD) and PtdCho-specific phospholipase D (PC-PLD, *Streptomyces chromofuscus*) is obtained from Biomol International (Plymouth Meeting, Pa.). Type IA sPLA2 (*naja mossambica mossambica*), type IB sPLA2 (porcine pancreas), PC-PLC, PI-PLC and sphingomyelinase (SMase, *Bacillus cereus*) are obtained from Sigma (St. Louis, Mo.).

Liposome and Fluorophore Lipid Dispersions

Liposomes were prepared by aliquoting PtdCho, PtdCho:PtdEtn:Chol (2:1:1) or PtdCho:Sph:PtdGro:Chol (5:5:1:2) into glass tubes, evaporating chloroform under dried $N_2$, followed by drying under vacuum. The resulting film is resuspended in buffer (50 mM Tris-HCL, pH 7.4), sonicated and vortexed for 5 min, followed by extrusion 8-10× through the Avanti Polar Lipids Extruder using the 100 nm membrane. NIR-fluorophores are solubilized in chloroform and concentration determined by measuring the absorbance at 418 nm using the Beer-Lambert law (OD=ε 1 c). The fluorophores (20-80 nmoles) are combined with the appropriate mixture of phospholipids in chloroform at MF=0-0.05, dried under a stream of $N_2$ and treated as above. For Tween preparations, 20-80 nmoles of fluorophore is dried under $N_2$ and Tween-80 is added to a final concentration of 0.1%. The solution is resuspended in 200 µL of 50 mM Tris-HCl, pH 7.4, vortexed and sonicated for 10 min.

A measured amount of Pyro-PL-BHQ or Pyro-PL (ε=110,000 $M^{-1}$ $cm^{-1}$ at 410 nm) was combined with PtdCho (chicken egg, Avanti Polar Lipids, Inc., Alabaster, Ala.) in chloroform and dried under a stream of nitrogen. Lipid films were rehydrated with buffer (50 mM Tris-HCL, pH 7.4) and small unilamellar vesicles were formed by sonication in a bath sonicator until an optically clear dispersion was obtained.

Specificity and Sensitivity

Fluorophores were prepared in lipid vesicles at 1 µM fluorophore-BHQ in PtdCho vesicles (MF=0.05). Aliquots of fluorophore/lipid dispersions are incubated at 37° C. with 1 unit of enzyme. After 6, 24 or 48 hours, a sample from each aliquot is separated on a UV Silica Gel TLC plate using the solvent chloroform:methanol (100:15). Fluorescent bands due to cleavage were detected using an UV lamp at 385 nm and compared to starting materials or control fluorophores/lipid dispersion. Phospholipases that exhibit an ability to cleave the self-quenching NIR fluorophores were assayed for sensitivity by measuring the rate of released fluorescence after the addition of 1 unit of enzyme with a Molecular Devices Spectra Max Gemini fluorescent plate reader (ex, 418 nm; em, 675 nm). Reaction mixtures are allowed to equilibrate to 37° C. and phospholipase are added in buffer to a total volume of 100 µL.

Enzyme Kinetics

Phospholipase (0.5 to 5 units) are added to 1 µM fluorophore-BHQ in PtdCho vesicles (MF=0.05) to yield a final volume of 100 µL. Initial velocities are measured as a function of enzyme concentration. For bulk kinetics, an enzyme concentration that gives a linear response is chosen. The lipid dispersions is diluted in buffer such that the fluorophore-BHQ concentration varies from 0.3-3 µM. The temperature is held at 37° C. and phospholipase added to a total volume of 100 µL. The released fluorescence is measured and the initial velocities recorded as a function of bulk lipid concentration. A Lineweaver-Burke plot of 1/V0 vs 1/[S] gives a straight line with slope −1/Km and y intercept of 1/Vmax. For interfacial kinetics, lipid dispersions of fluorophore-BHQ and PtdCho are diluted in Triton X-100 with the total lipid concentration held at 20 µM. The ratios of fluorophore-BHQ to PtdCho are held constant, but varied relative to the MF of Triton with a total MF of fluorophore-BHQ of =0.01-0.05). Initial velocities are recorded as a function of concentration, and kinetic parameters are calculated.

Calibration

The permanently fluorescent phospholipids are used as an analog to the fluorescent products released by PL cleavage. For example, Pyro-PL-BHQ and Pyro-PL is mixed at a MF of 0.003 in PtdCho vesicles, such that the concentration of ([Pyro-PL]+[Pyro-PL-BHQ]) is held constant at 100 pmoles. Pyro-PL is incremented from 0-25 pmoles and the Pyro-PL-BHQ concentration adjusted. Fluorescence intensity is measured as a function of concentration in order to convert emission/sec to pmoles/sec.

Subcutaneous Tumor Growth

DU145 or WSU-DLCL2 cells (5×10⁶) are injected subcutaneously into the flanks of 4-6 wk old athymic nude mice or SCID mice respectively (NCI, Fort Dietrich, Md.). Tumors are studied from when they reach a volume of about 200-400 µm³, which is 7-9 wks after implantation for DLCL2 tumors, 4-6 weeks for DU145.

In Vivo ¹H MRS

In Vivo NIR Fluorescence Imaging

DU145 cells (5×10⁶) were injected subcutaneously above the left hind legs of 4-6 week old athymic nude mice (NCI, Fort Dietrich, Md.). Tumors were grown until they reached a volume of 200-400 μm³, which is 4-6 weeks for DU145. Mice were fed low-fluorescent pellets (Labdiet 5V02, Animal Specialties and Provisions, LLC, PA) for 1-3 days prior to imaging Mice were anesthetized with 100 μL ketamine (50 mg/ml)/acepromazine (5 mg/ml). Prescan visible and fluorescent images were taken with a Xenogen IVIS system using Cy5.5 fluorescence filters ($\lambda_{ex}$=615-667 nm, $\lambda_{em}$=695-770 nm), and an exposure time of 1 s. Following the prescan image, the mice were injected i.v. with 80 nmol Pyro-PL or Pyro-PL-BHQ solubilized in buffer (50 mM Tris-HCl, pH 7.4) and 0.1% Tween-80 (200 μL/mouse) and returned to the Xenogen. Images were acquired every few minutes for the first 1.5 h, followed by every hour up to 6 h, and then again between 24 h and 30 h. Background fluorescence was subtracted from all images. A region of interest (ROI) was drawn around both the tumor and the contralateral muscle and the average radiance was measured as the total fluorescence flux normalized to photons per second per centimeter squared per steradian (photons/s/cm²/sr). The tumor:muscle average radiance ratios were calculated at each time point.
HPLC MALDI-TOF Products of the Pyro-PL-BHQ-phospholipase cleavage experiments were separated using reverse-phase HPLC. The HPLC system consisted of a Waters 600 controller with quaternary pump, and equipped with a Waters 2996 diode array detector (Waters Corp, Milford, Conn.) and a Zorbax 300SB-C3 column (4.6×150 mm, Agilent Corp, Santa Clara, Calif.). The flow rate of the mobile phase was 1.5 mL/min. The mobile phase composition was: (A) acetonitrile, (B) 0.1 M TEAA (triethylamine+acetic acid, pH=7), and (C) methanol. Solvent composition began with 80% solvent A and 20% solvent B, which was increased to 90% A and 10% B over 10 min Conditions were then changed to 90% A and 10% C for 10 min followed by 90% C and 10% A over 60 min. The identity of isolated fragments was confirmed with MALDI-TOF MS using an Applied Biosystems Voyager DE Mass Spectrometer with positive mode ionization. The matrix consisted of α-cyano-4-hydroxycinnamic acid or 2-(4-hydroxyphenylazo) benzoic acid.
Statistical Analysis.

All data are presented as mean±s.d. Statistical analysis of in vivo tumor:muscle average radiance was conducted using Student's t-test. The test performed was two-tailed when testing Pyro-PL against Pyro-PL-BHQ (±D609) and one-tailed when testing Pyro-PL-BHQ against Pyro-PL-BHQ+D609. A p value≤0.05 was considered to be significant.

Example 1: Synthesis of Self-Quenching Phospholipid-Based Molecular Beacons

A series of phospholipid analogs containing an NIR fluorophore and quencher pair that can be activated by specific phospholipases were developed. For NIR fluorophores (NIRF), we have chosen two neutral porphyrins, pyropheophorbide a (Pyro, e6 ($\lambda$ex=665, $\lambda$em=725 nm) and bacteriochlorin (Bchl, $\lambda$ex=750, $\lambda$em=785 nm; see FIG. 1). Pyro is a chlorophyll a derivative that we isolate from *Spirulina Pacifica* at a yield of about ~6 g per 7.5 kg algae. Bchl is derived from bacteriochlorophyll isolated in house from *Rhodobacter sphaeroides*. These porphyrin-based fluorophores have a number of qualities that make them ideal for incorporation into fluorescent NIR lipid analogs. They are both neutral and hydrophobic, two qualities that are essential for the incorporation into the sn-1 or sn-2 acyl chain positions. They have Stoke's shifts of 35 nm or greater and their frequencies of absorption and fluorescence are generally unaffected by solvent or environment. Porphyrin fluorophores also have the ability to non-specifically accumulate in tumors. Since the aim is to design probes to assess phospholipid metabolism in a range solid tumors, this targeting mechanism provides an additional advantage. However, phospholipids containing porphyrin fluorophores will not spontaneously form membranes: the planar molecules can stack leading to fluorescence quenching. Thus for in vitro or in vivo delivery, the fluorescent porphyrin-containing probes must be encapsulated in liposomes or micelles.

For quenchers, the Black Hole quencher 3 (BHQ3; Bioresearch Technologies, Novato, Calif.) and the BlackBerry quencher (BBQ-650; Berry and Associates, Dexter, Mich.) are used. Both BHQ and BBQ dyes are high-efficiency dark quenchers (i.e. no native fluorescence) with a broad absorption spectrum resulting in much larger signal-to-noise ratios.

Example 2: Enzymatic Hydrolysis of PYRO-PL-BHQ Yields a Fluorescent Product

In Pyro-PL-BHQ, BHQ acts as an effective quencher of Pyro fluorescence, reducing the fluorescence emission relative to Pyro-PL between 25-fold (for $\lambda$ex=675, $\lambda$em=725 nm) and 45-fold (for $\lambda$ex=418, $\lambda$em=695 nm). In PyroPyro-PL, quenching is less efficient (~4 fold) since the acceptor molecule, a second Pyro, is not dark. This limits the usefulness of this compound as an in vivo probe. However, PyroPyro-PL was used to develop the method for insertion of Cm spacers for synthesis of highly efficient NIR detectors of PLA2 activity and incorporation of the neutral BBQ quenchers onto the sn-1 or sn-2 positions.
Specificity and Sensitivity Although PC-PLC, SMase and PLD all demonstrated the ability to hydrolyze Pyro-PL-BHQ, observation of these reactions by fluorescence spectroscopy revealed that Pyro-PL-BHQ exhibited a remarkable sensitivity for PC-PLC (FIG. 2A). The addition of enzyme (10 U) to 1 μM Pyro-PL-BHQ dispersed in egg-PtdCho vesicles at a mole fraction (MF) of 0.02 led to a 30-fold increase in fluorescence within 5 min. In contrast, the fluorescence released by PC-PLD and SMase was negligible, even after 1 h. The Lineweaver-Burke for Pyro-PL-BHQ is presented in FIG. 3C. As shown in FIG. 2B, the hydrolysis by PC-PLC was able to fully restore Pyro-PL-BHQ fluorescence. The complete cleavage of Pyro-PL-BHQ resulted in a ~150-fold fluorescence increase, the expected increase of Pyro-PL fluorescence over that of Pyro-PL-BHQ at equal concentrations.

The dependence of activity on enzyme concentration was determined by adding increasing amounts of PC-PLC to 1 μM Pyro-PL-BHQ in egg-PtdCho dispersions (MF 0.003). The activity of PC-PLC with Pyro-PL-BHQ was measured as the rate of relative fluorescent units per minute (RFU/min), shown in FIG. 2C. Activity increased with enzyme concentration (mg) and was linear up to 0.002 mg (0.5 U) of enzyme.

Figure 3A:
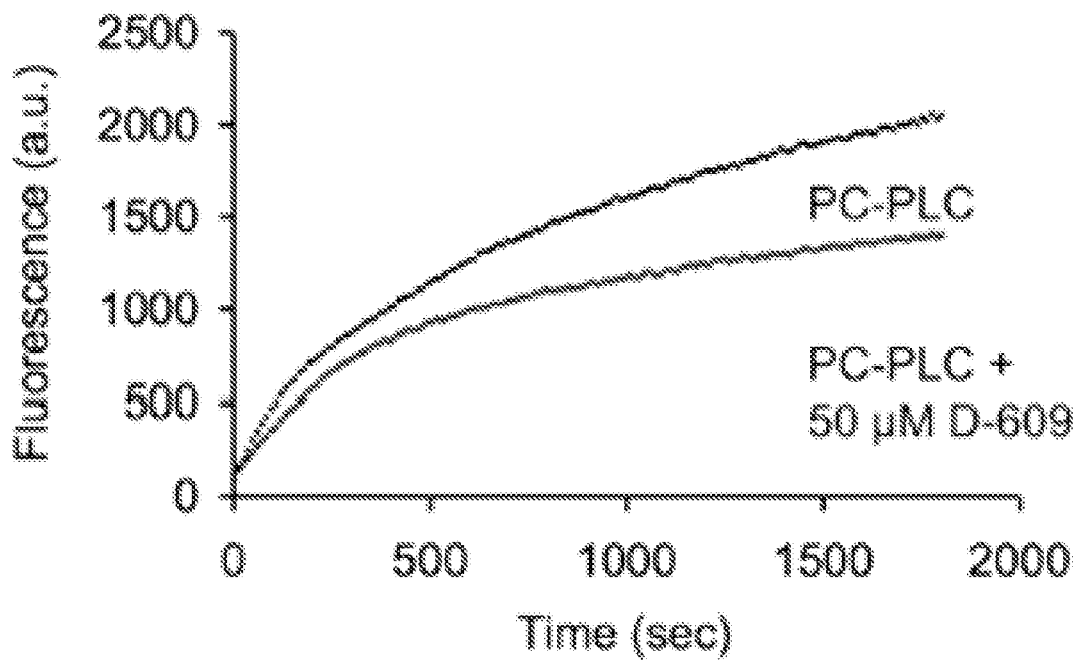
FIG. 3 shows time-dependent release of fluorescence from Pyro-PL-BHQ/PtdCho vesicles (A) Fluorescence release from Pyro-PL-BHQ is inhibited by the PC-PLC inhibitor D-609. (B) Initial rate was measured as a function of bulk lipid concentration in vesicles of Pyro-PL-BHQ in PC (MF=0.05) (C) Bulk Kinetics. Lineweaver-Burke for Pyro-PL-BHQ Kmapp=30.4 mM. Vmaxapp=1.96 nmoles $min^{-1}$ $mg^{-1}$. (D) Lineweaver-Burke plot of inhibition using 8, 50, 100 µM D609. A plot of Km(app)/Vmax(app) vs. D609 gives −Ki at the x-intercept (Ki=250 µM).
Figure 3B:
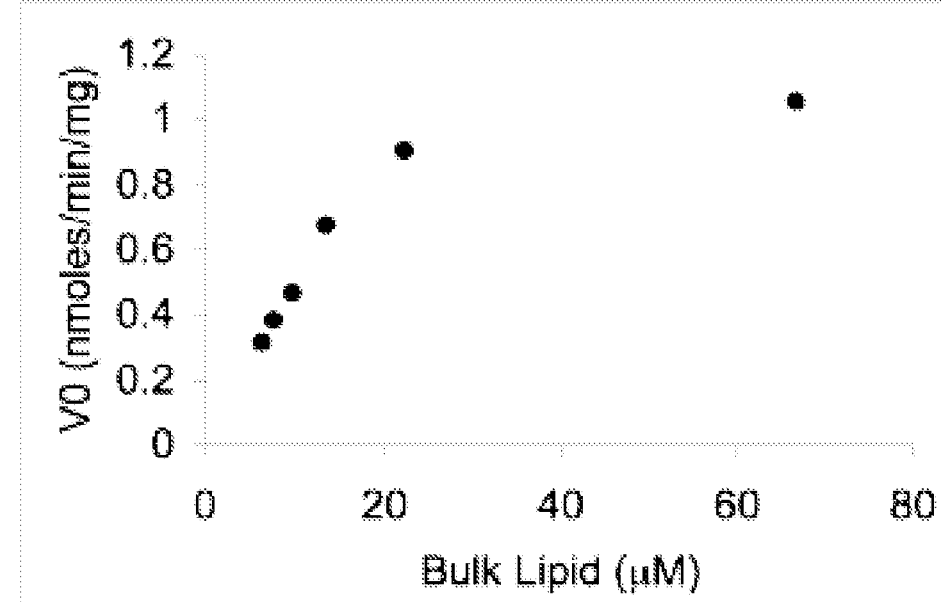
Figure 3C:
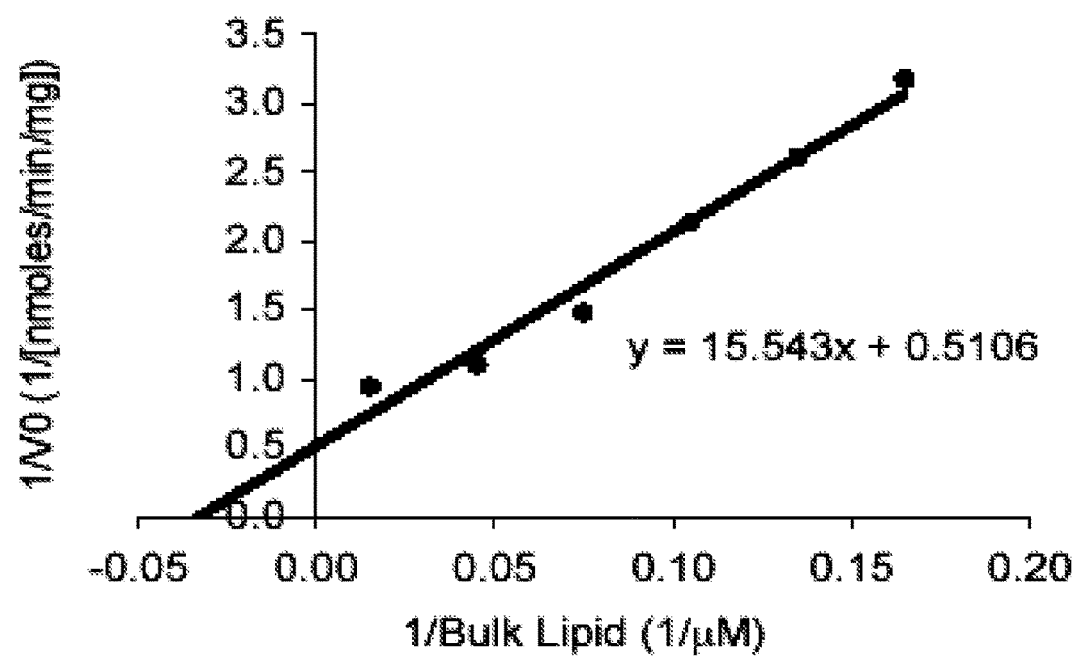
Figure 3D:
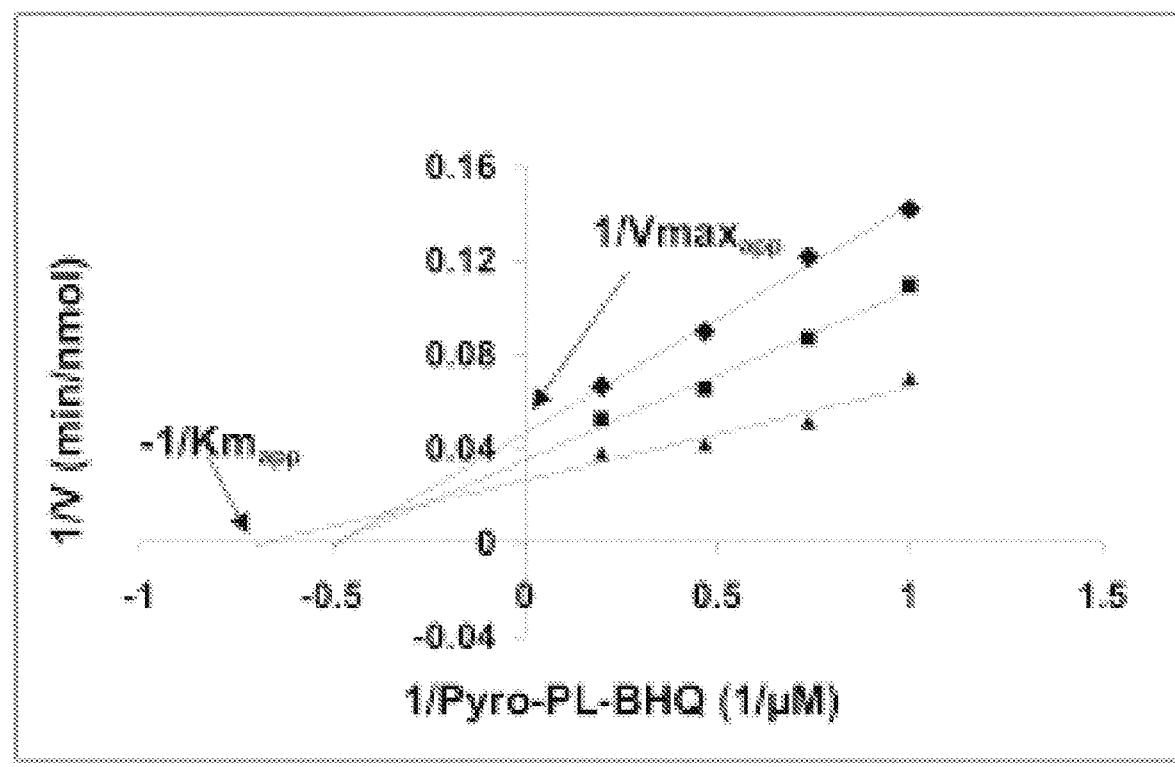

The rate of Pyro-PL-BHQ hydrolysis (MF 0.003 in egg-PtdCho dispersions) could be inhibited by D609, a specific PC-PLC inhibitor (FIG. 3A). Activity, in RFU/min/mg, was measured as a function of D609 concentration after the addition of 0.5 U PC-PLC (FIG. 2D). Complete inhibition was achieved with 500 μM D609 and an $IC_{50}$ of 34±8 μM was determined. A Lineweaver-Burke plot of inhibition is presented in FIG. 3D.

These data demonstrate that i) phospholipase-activated NIR beacons can be chirally synthesized; ii) the Pyro-fluorescence can be effectively quenched by conjugation with BHQ-3 and iii) Pyro-PL-BHQ displays remarkable sensitivity to PC-PLC indicating that specificity for particular enzyme classes can be achieved.

Thus, Pyro-PL-BHQ is well-suited for the detection of PC-PLC activity, both in its specificity and sensitivity for the enzyme. The strong increase in fluorescence upon enzymatic hydrolysis and the NIR attributes of this probe makes it an excellent candidate for in vivo optical imaging that can be used in tandem with magnetic resonance spectroscopy (MRS). This NIR probe is the first of several NIR phospholipase probes that facilitate the ability to directly monitor specific catabolic pathways in choline metabolism, thus leading to a greater understanding of the role of MR-visible metabolites in cancer.

Figure 4A:
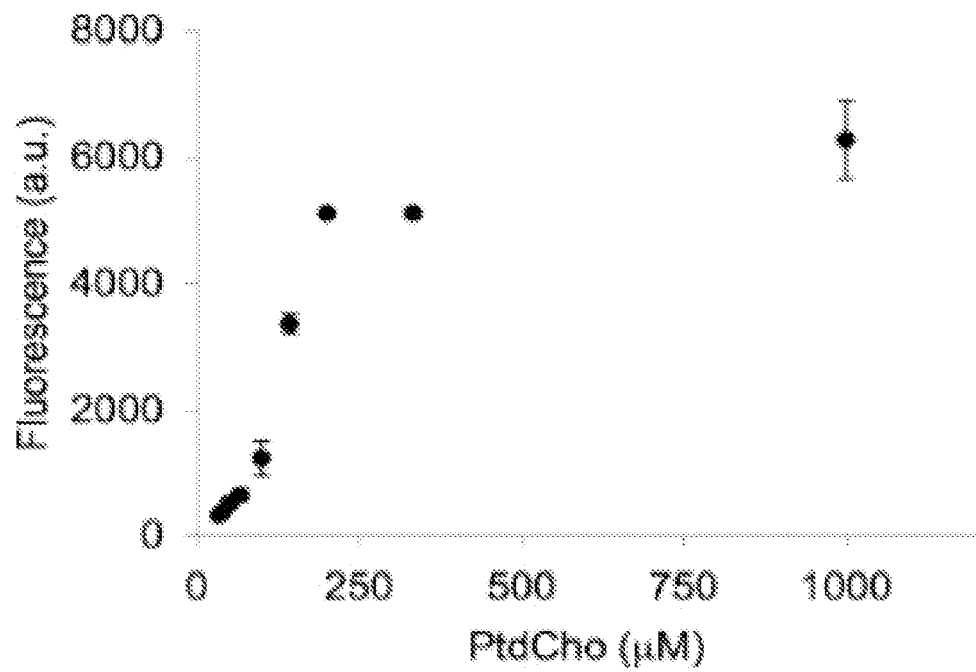
FIG. 4 shows (A) Incorporation into PtdCho vesicles. Fluorescence was recorded at varying [PtdCho], with [Pyro-PL] held constant at 1 µM. The fluorescence intensity increases as the Pyro-PL disperses into the vesicles and plateaus at the point at which self quenching, and therefore, aggregation is negligible. The plateau occurred at [PtdCho] >200 µM corresponding to Pyro-PL MF<0.005. (B) Calibration Curve. The concentration of Pyro-PL was mixed with Pyro-PL-BHQ at a MF of 0.003 in PtdCho vesicles, such that the concentration of ([Pyro-PL]+[Pyro-PL-BHQ]) was held constant at 100 pmoles, this was compared to pyro-PL incremented from 0 to 25 pmoles in the absence of Pyro-PL-BHQ. This was used to convert a.u./sec to pmoles/sec.

In order to determine the mole fraction (MF) at which all fluorophore can be assumed to be completely incorporated and intercalated into the PtdCho vesicles, an experiment was conducted in which the concentration of PtdCho was varied while Pyro-PL concentration was held constant at 1 µM (FIG. 4A). The fluorescence intensity increases as the Pyro-PL disperses into the PtdCho vesicles. The fluorescence plateaus at the point at which aggregation is negligible. Incorporation was found to occur at PtdCho concentration of greater than 200 µM corresponding to Pyro-PL MF<0.005.

Figure 4B:
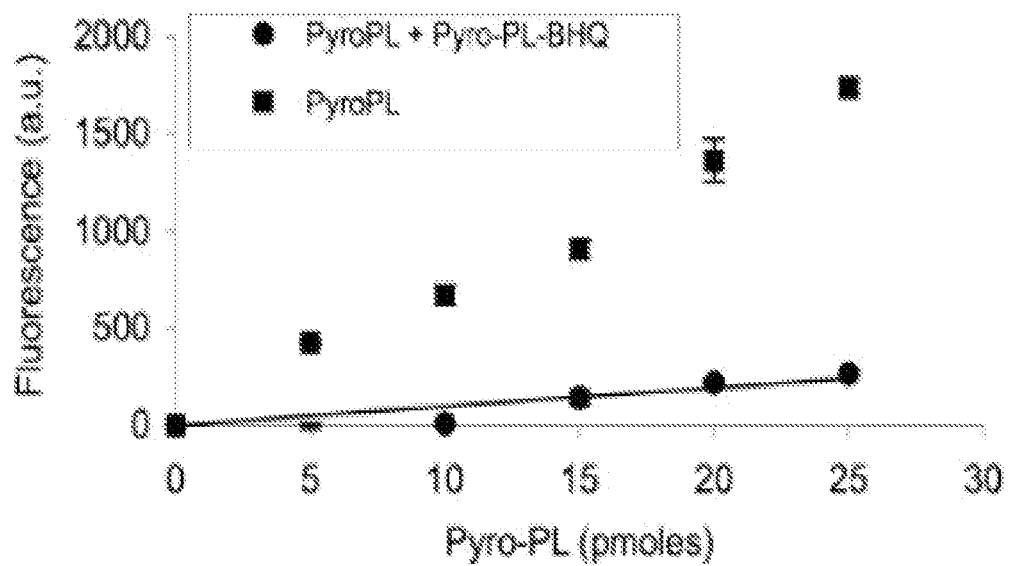

A calibration curve was constructed to determine the effects of intermolecular quenching in Pyro-PLBHQ vesicles. To do this, a Pyro-PL standard curve was first constructed by varying the fluorophore concentration in the tube while keeping the MF constant at 0.003 (FIG. 4B, squares). This curve was compared to one in which Pyro-PL was mixed with increasing concentrations of the quenched fluorophore, Pyro-PL-BHQ, keeping the total fluorophore concentration and the MF constant. If intermolecular quenching was negligible, then the two curves should superimpose. The substantial decrease in fluorescence observed in Pyro-PL/Pyro-PL-BHQ mixtures indicates that there is an important contribution from intermolecular quenching. This correction factor was applied to future assays to estimate concentrations.

Bulk Michaelis-Menten Kinetics.

Figure 5:
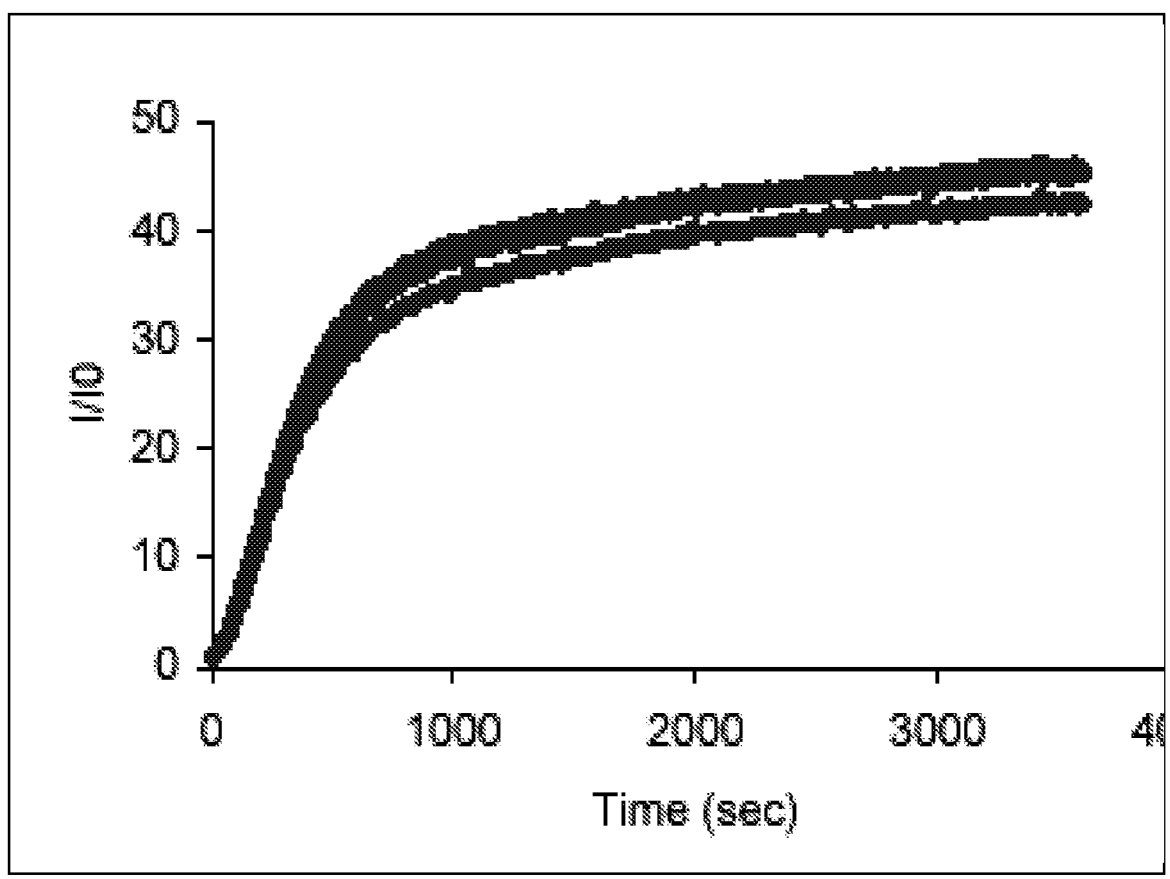
FIG. 5 shows a time-dependent plot of relative fluorescence intensity wherein the fluorescence intensity of cleaved substrate at t ∞ is 40-fold greater than the quenched substrate.

The activity was linearly proportional to enzyme concentration in the region of 0 to 0.005 mg of enzyme (FIG. 2C), and 0.0025 mg enzyme was used in all further assays. Initial rates were estimated from the time-dependent plots of relative fluorescence (FIG. 5). Note in this figure the consistency achieved between different experiments. Note also that the fluorescence intensity at G is 40-fold greater than the quenched substrate, as would be predicted from FIG. 2A. To determine the Michaelis-Menten kinetic parameters (Km, Vmax), initial reaction rate was measured as a function of bulk lipid concentration in vesicles of Pyro-PL-BHQ in PtdCho (MF=0.05) (FIG. 2C). The initial rate was taken during the steady state region. An apparent Km=30.4 µM and Vmax=1.96 nmoles min-1 mg-1 were observed, as determined from the Line weaver-Burke plot (FIG. 5).

Example 3: Cell Uptake Studies

Figure 6:
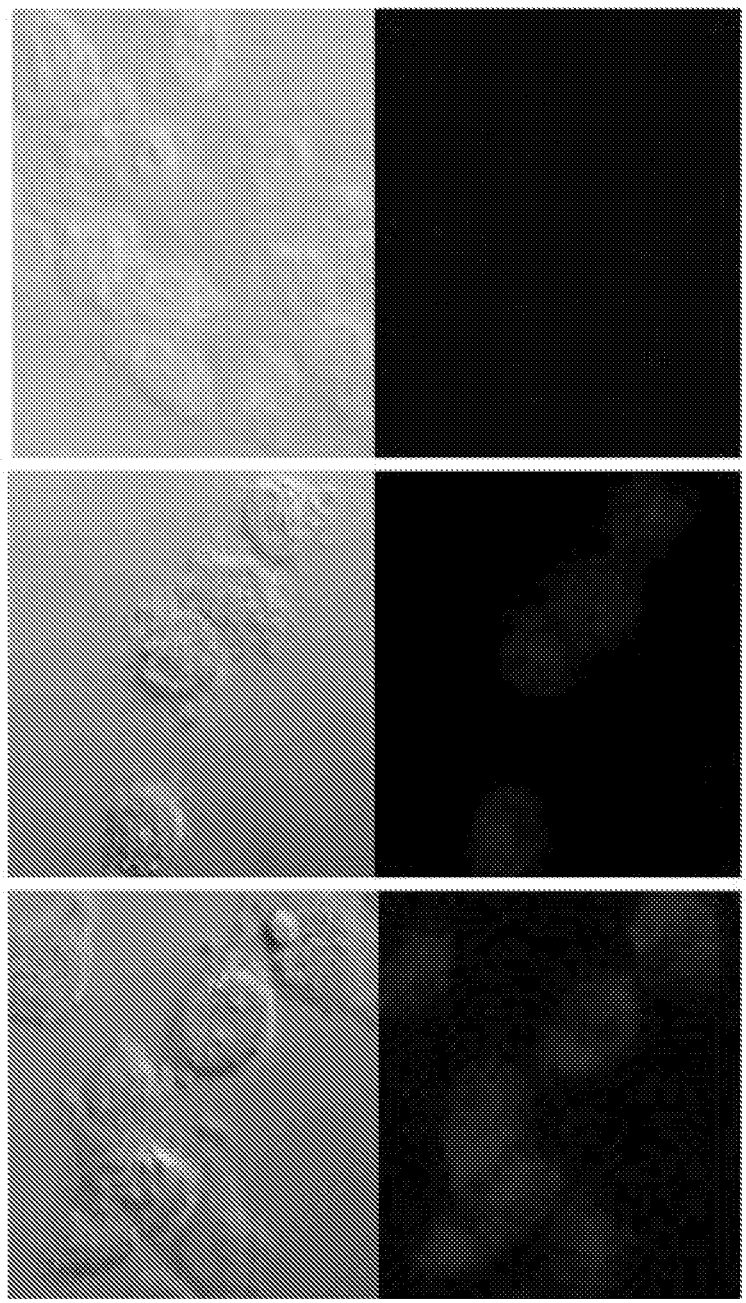
FIG. 6 shows bright field and confocal micrographs of uptake of Pyro-labeled phospholipid in DU145 cells. (A) Fluorescent Pyro-PL, localizes primarily in cytoplasm. (B) Pyro-PL-BHQ, no treatment. (C) Pyro-PL-BHQ activation after 6 h treatment with 10 mM PB, 6 h. The red fluorescence represents the release of Pyro from Pyro-PL-BHQ.

In an experiment to test whether Pyro-PL-BHQ could be activated in situ, DU145 prostate cells were incubated for 1 hr in the presence of 5 µM Pyro-PL, Pyro-PL-BHQ or PBS as control and observed by laser confocal microscopy. FIG. 6 shows that the localization of the permanently fluorescent Pyro-PL is primarily cytoplasmic. Weaker fluorescence is observed in cells incubated with Pyro-PL-BHQ, but the fluorescence is increased by the addition of PB, a differentiating agent that we have shown to affect tumor lipid metabolism.

Figure 7:
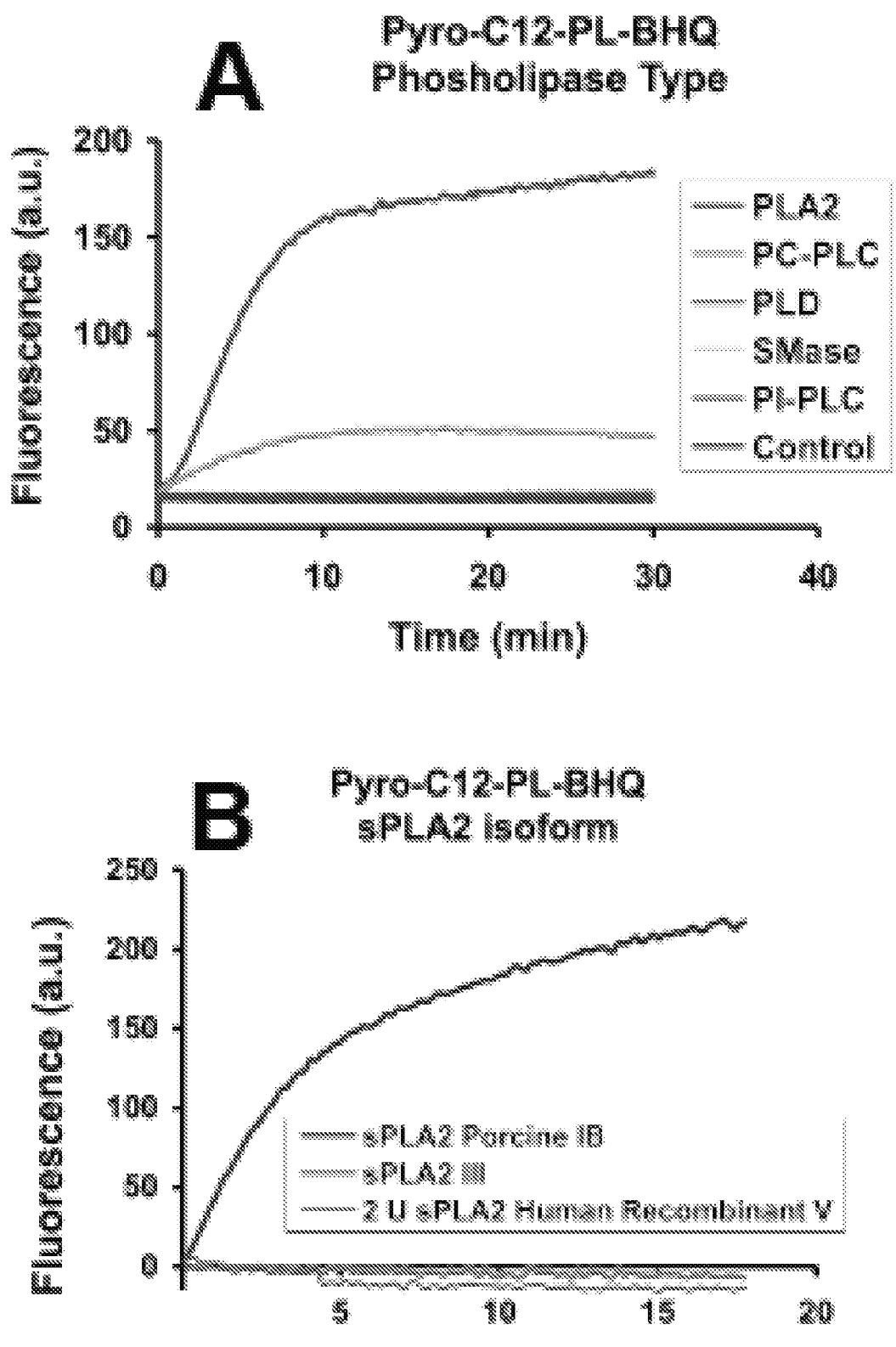
FIG. 7 shows the sensitivity and specificity of Pyro-C12-PL BHQ. The top two panels show the phospholipase type (A) and isoform (B) specificity of Pyro-C12-PL-BHQ and demonstrates the specificity to sPLA2 Type 1B.

Example 4: Characterization of Pyro-C12-PL-BHQ, a Specific Phospholipase A2 Activated Fluorescent Probe Pyro-C12-PLBHQ, the first NIR phospholipase A2 sensitive probe was synthesized and partially characterized. FIG. 7A shows that the spacer in Pyro-C12-PLBHQ imparts an increased specificity to PLA2 relative to other phospholipase types. FIG. 7B demonstrates that of the three PLA2 isoforms tested so far, this probe displays remarkable specificity to sPLA2 1B.

Example 5: In Vivo Activation of Pyro-PL-BHQ

Figure 8:
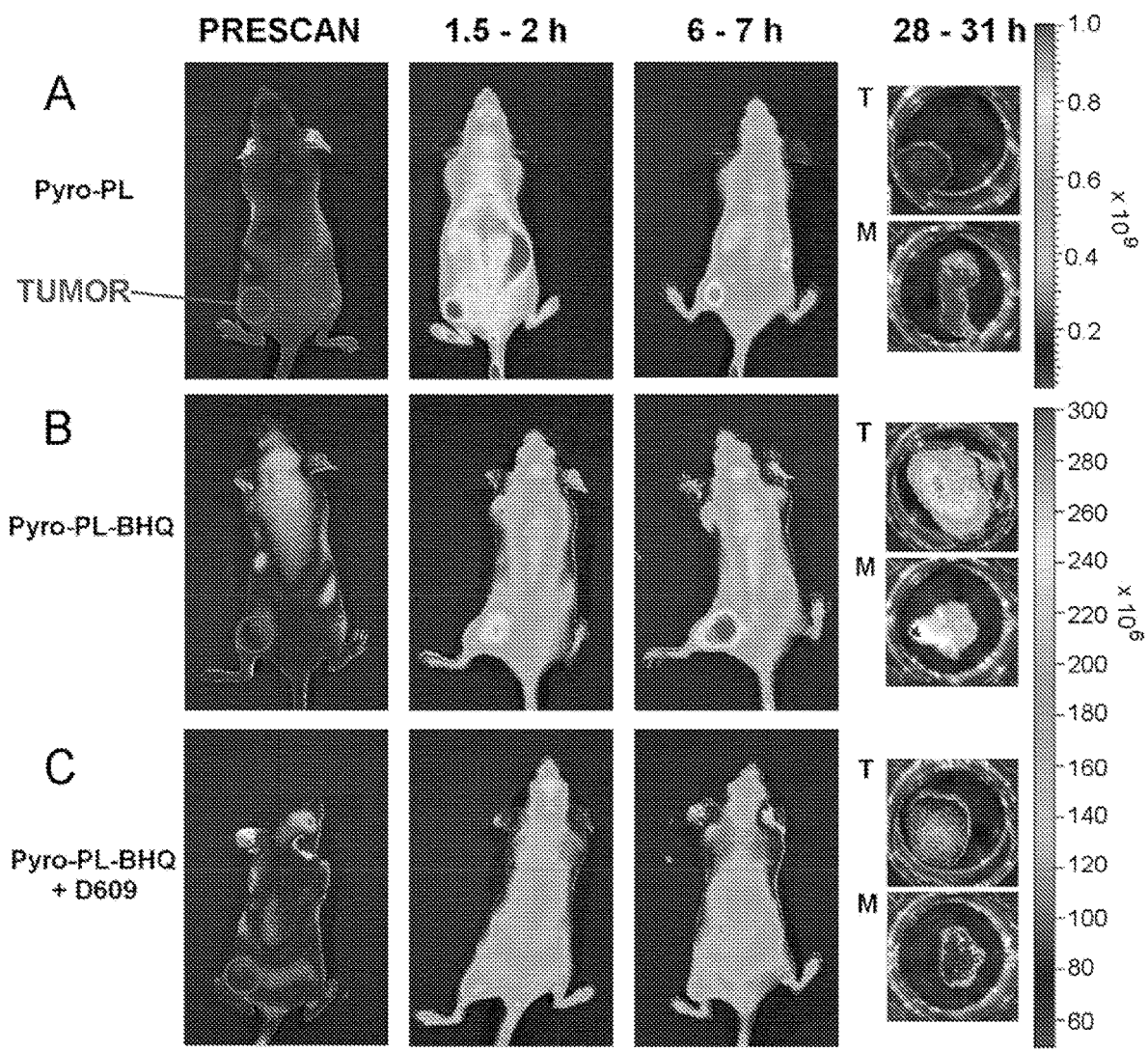
FIG. 8 shows the in vivo detection of PC-PLC activity. Mice bearing DU145 tumors were injected with (A) Pyro-PL (B) Pyro-PL-BHQ or (C) Pyro-PL-BHQ+D609. The fluorescent Pyro-PL showed wide dispersion throughout the body, accumulating in the liver and gut whereas fluorescence from the activatable Pyro-PL-BHQ was observed primarily in the tumor. The PC-PLC inhibitor D609 significantly reduced Pyro-PL-BHQ tumor fluorescence.

Nude mice bearing DU145 tumor xenografts on the left hind flank were injected with Pyro-PL-BHQ (80 nmol dispersed in 0.1% Tween80) or the permanently fluorescent Pyro-PL as a positive control. Pyro-PL exhibited fast circulation throughout the body, accumulating primarily in the stomach, liver, and intestines (FIG. 8A). By 6 h, the substrate was being cleared through the digestive tract, as fluorescence was observed solely in the small intestine. Injection of Pyro-PL-BHQ led to a gradual increase in tumor fluorescence within 1.5 h (FIG. 8B) with persisting high tumor fluorescence at 7 h post-injection. Improvements in the purification procedure, using a double round of preparative TLC, removed fluorescent impurities and markedly reduced the Pyro-PL-BHQ digestive tract fluorescence reported in the previous submission of this application. The PC-PLC inhibitor D609 was used to validate that tumor Pyro-PL-BHQ fluorescence was due to enzyme activation. Due to its short half-life, D609 was administered (50 µg/g body weight, i.p.) to mice 30 min pre- and 30, 60, and 120 min post-injection of Pyro-PL-BHQ. D609 inhibited in vivo activation of Pyro-PL-BHQ, resulting in reduced tumor fluorescence (FIG. 8C).

Figure 9:
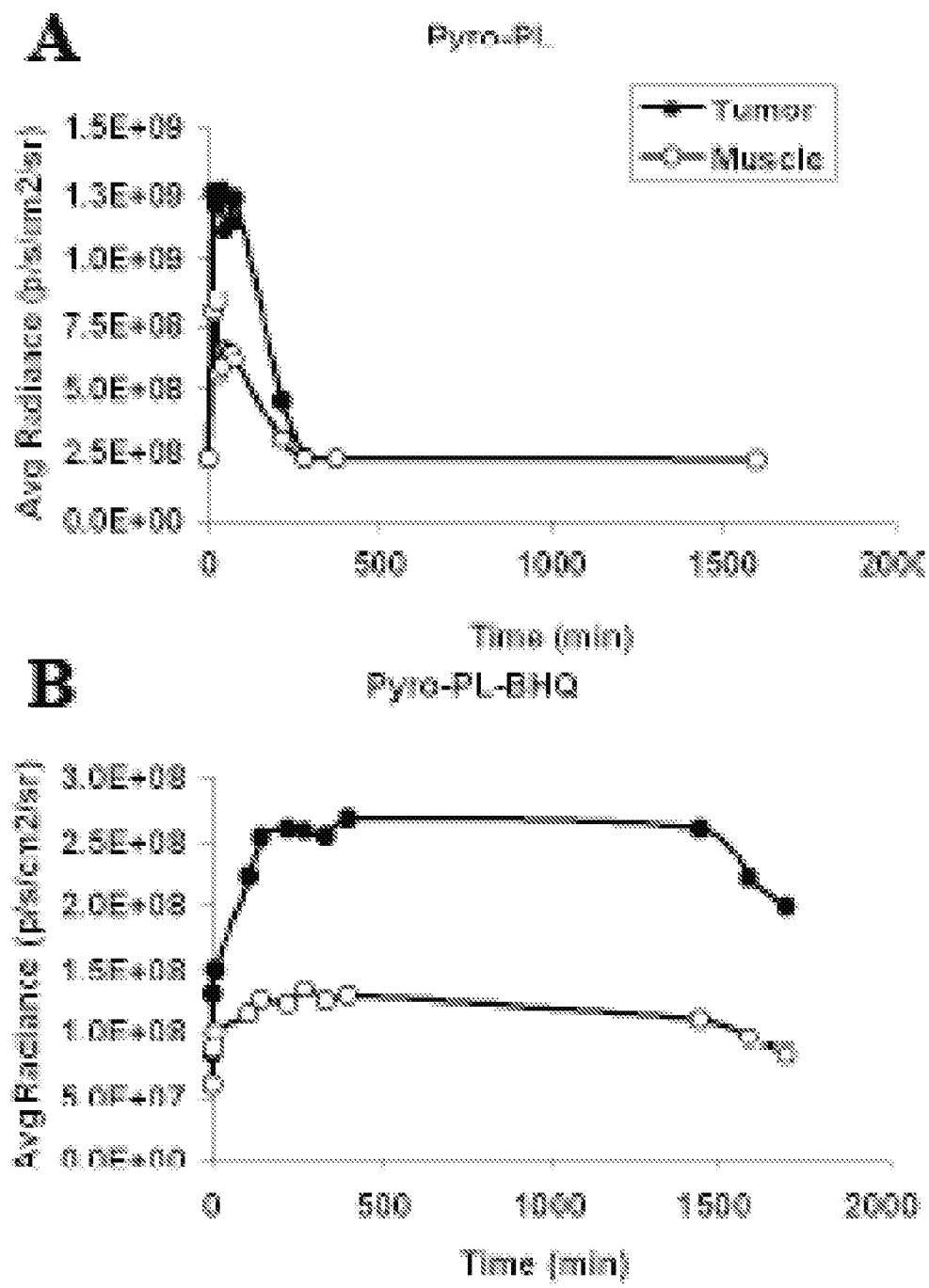
FIG. 9 shows tumor and muscle radiances. A ROI was drawn around the tumor and contralateral muscle tissue and the average radiance was quantified. Representative time course measurements are shown for (A) Pyro-PL (B) Pyro-PL-BHQ or (C) Pyro-PL-BHQ+D609. (D) Tumor:Muscle average radiance. The average tumor radiance was normalized to that of the contralateral muscle at 10 min, 1 h, 5 h and 24 h post-injection of Pyro-PL (n=3), Pyro-PL-BHQ (n=5) and Pyro-PL-BHQ+D609 treatment (n=3). Error bars represent standard deviation *Significantly (p≤0.05) different than Pyro-PL. † Significantly (p≤0.05) different than Pyro-PL-BHQ without D609 treatment.
Figure 9:
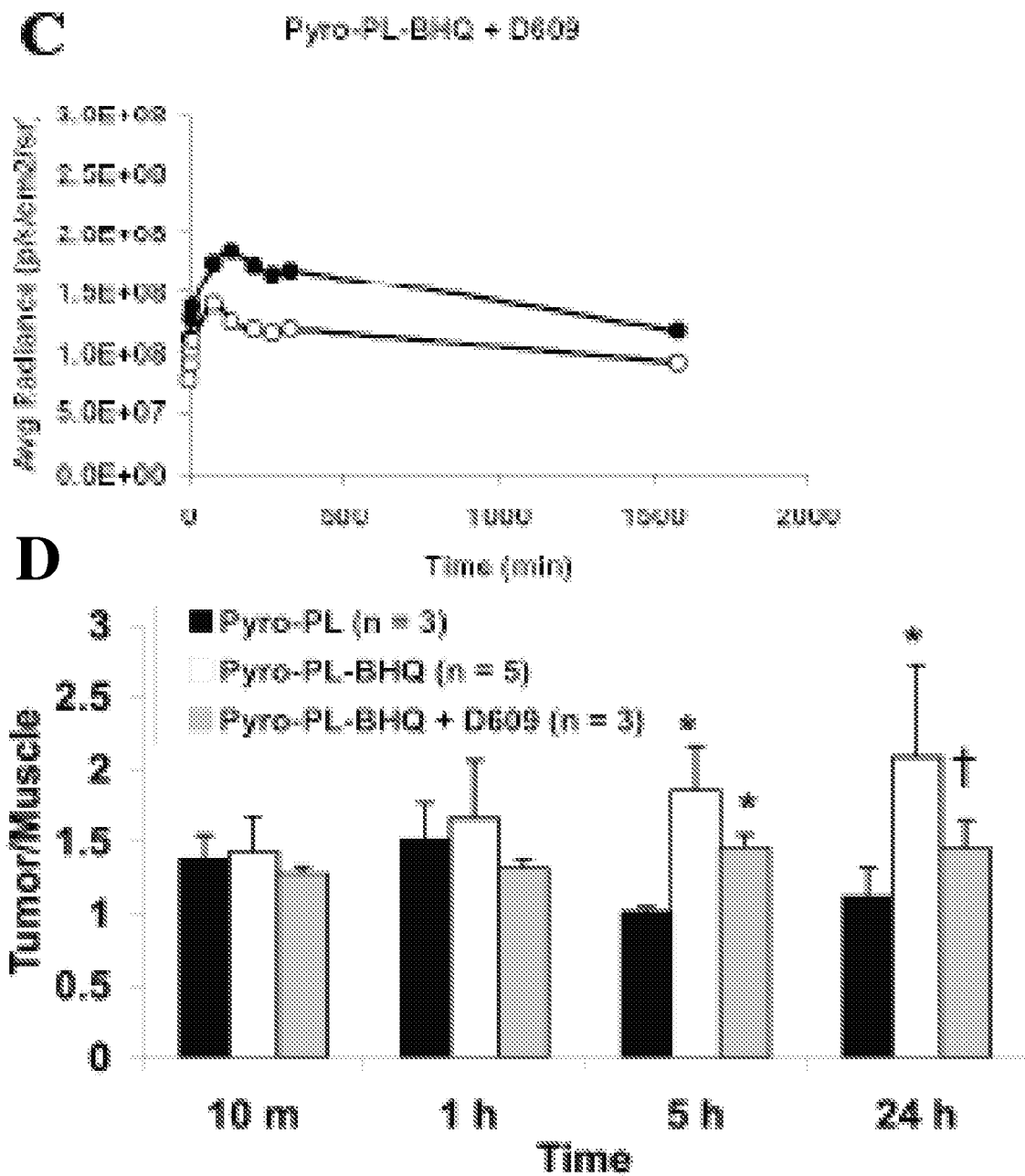

Representative time dependence of the average radiance for tumor and contralateral muscle are shown in FIG. 9A-C, respectively. Pyro-PL led to a sharp initial increase in both tumor and muscle radiance, reaching a maximum tumor radiance ~5-fold over baseline at 30 m post-injection, followed by wash-out, returning to prescan levels by 6 h post-injection (FIG. 9A). In contrast, Pyro-PL-BHQ tumor radiance gradually increased ~4-fold over baseline during the first four hours, and remained constant to 24 h before clearing from the tumor and returning to baseline by 28 h (FIG. 9B). The muscle radiance shows a small initial increase, plateauing within 10 min. From 2-24 h, the tumor radiance is about 2.5-fold greater than the contralateral muscle. Pre- and post-treatment with D609 caused an overall attenuation of tumor radiance as soon as 2 h after injection, and continued to suppress probe activation until clearance at 28 h (FIG. 9C). The average tumor:muscle radiance at 5 h was significantly ($p<0.05$) higher for Pyro-PL-BHQ than Pyro-PL (FIG. 9D). At 24 h, D609 treatment had significantly inhibited the activation of Pyro-PL-BHQ ($p<0.05$), decreasing the tumor:muscle average radiance back to baseline levels.

Figure 10:
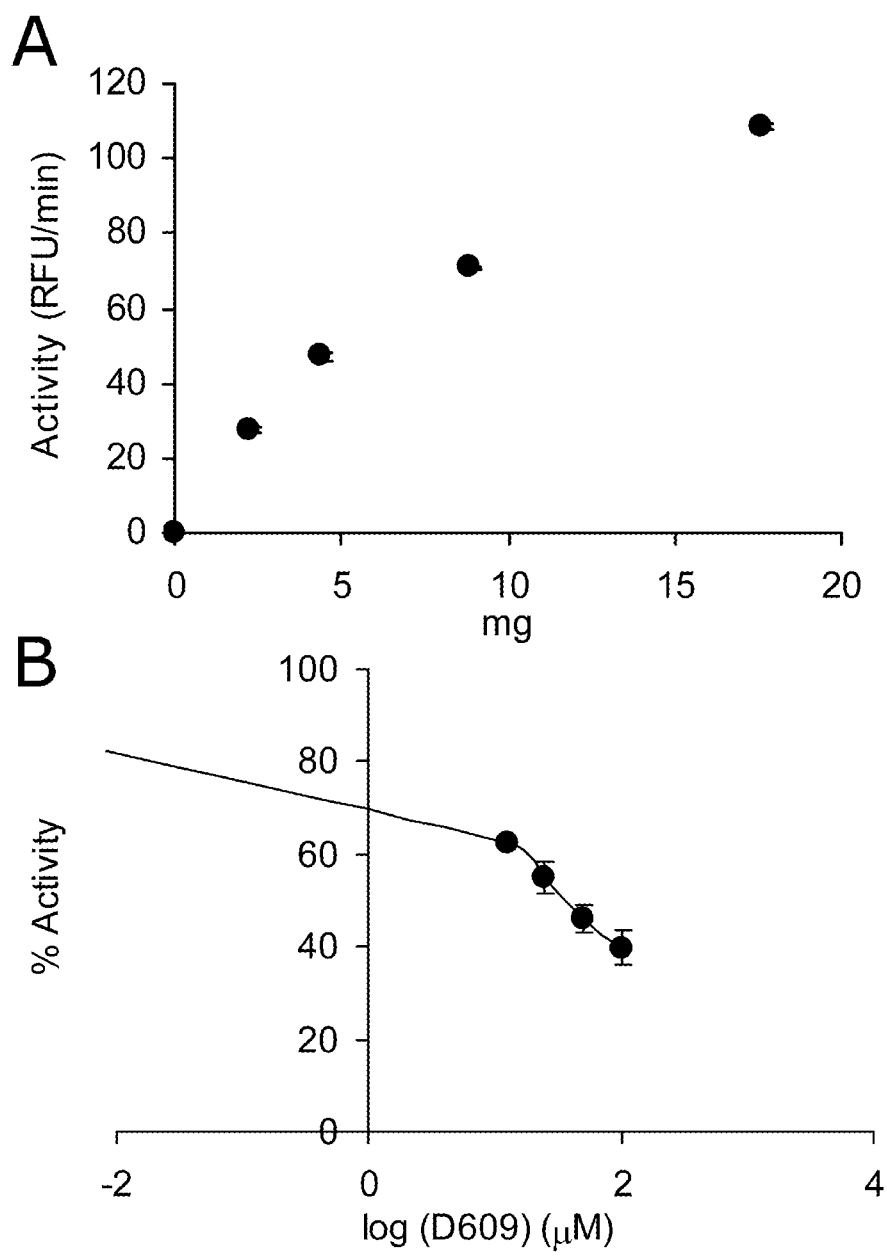
FIG. 10 shows PC-PLC activity measured by Amplex Red. PC-PLC activity measured by Amplex Red. (A) Activity (RFU/min) measured as a function of protein (mg) from extracts of DU145 tumor xenografts. (B) % activity measured as a function of D609.

To validate the presence of PC-PLC activity in DU145 tumor xenografts, the Amplex Red PC-PLC assay kit (Molecular Probes) was used to measure PC-PLC activity in extracts of excised tumors. Increasing amounts of supernatant yielded higher activities (RFU/min), as detected by increases in resorufin fluorescence (FIG. 10A). This activity was shown to decrease as a function of D609 concentration (FIG. 10B).

Example 6: In Vivo Distribution of NIRF Probes

Figure 11:
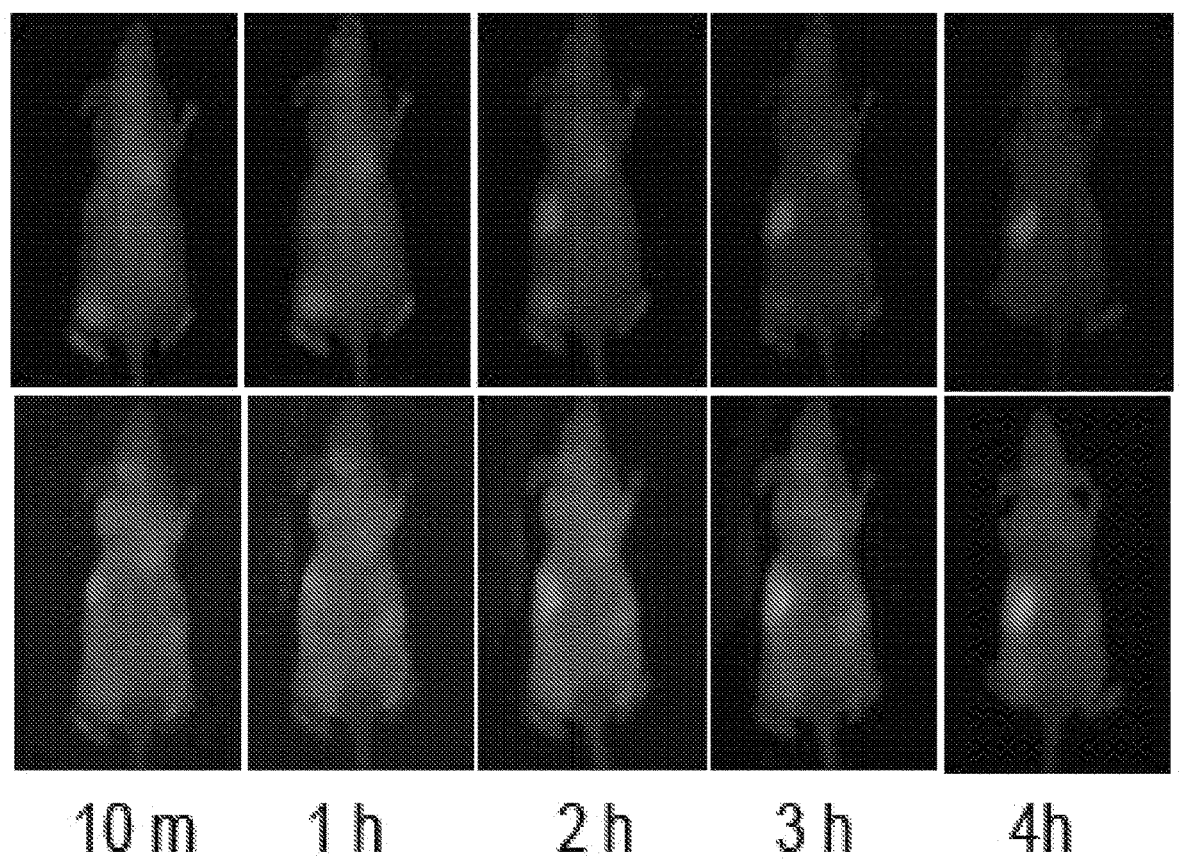
FIG. 11 shows the separation of Pyro-PL fluorescence from autofluorescence using spectral deconvolution on the Maestro system. The top images show total fluorescence, the bottom images show deconvoluted images with Pyro-PL fluorescence shown as red, autofluorescence as blue and co-localization as pink. Pyro-PL accumulates in the tumor as early as 10 min, persisting for up to 3 h, followed by co-localization in the gut with the autofluorescence.
Figure 12:
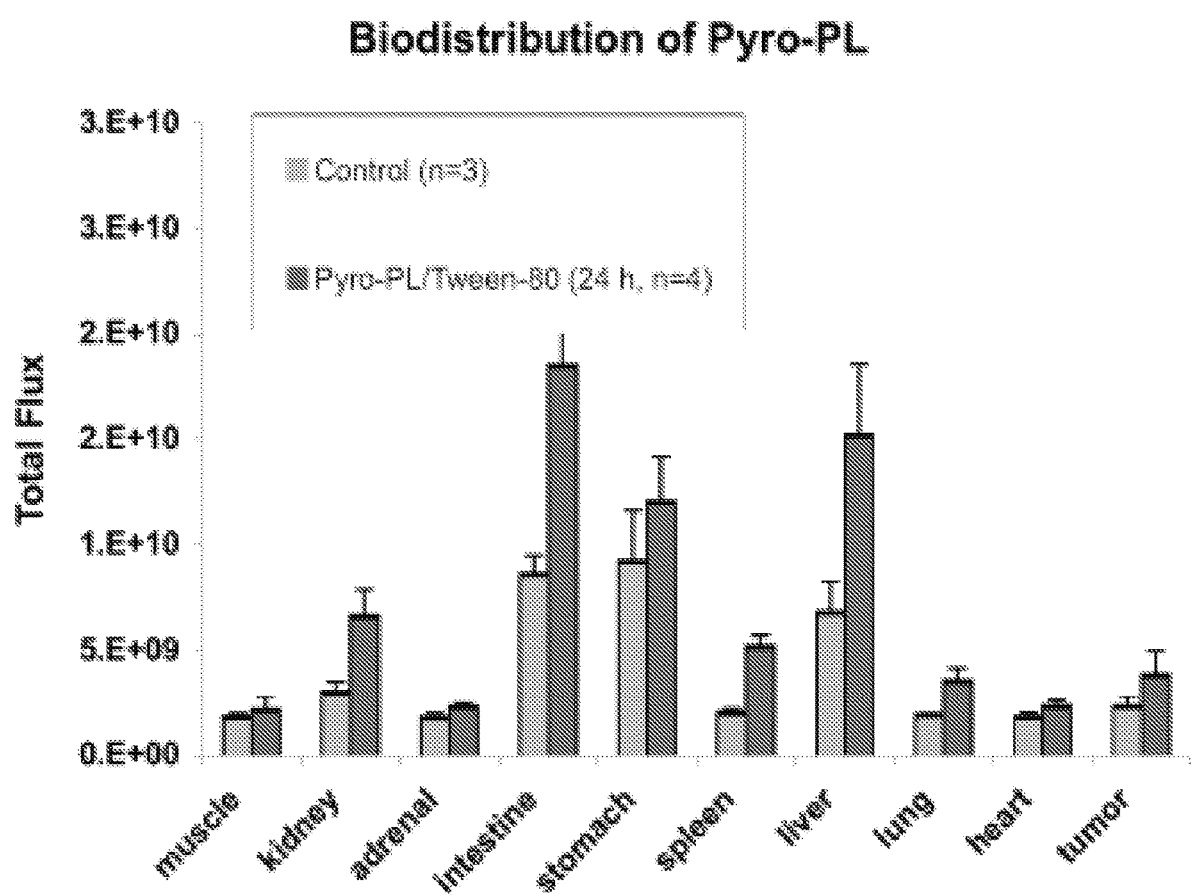
FIG. 12 shows nude mice bearing subcutaneous DU145 prostate tumors were injected i.v with Pyro-PL in 0.1% Tween-80. The mice were sacrificed at 24 h, the organs harvested and imaged with a Xenogen IVIS Imaging System. Control mice were not injected with Pyro-PL.

Methods for separation of probe fluorescence and autofluorescence have been developed that result in a more accurate detection of in vivo probe fluorescence. In FIG. 11, mice injected with the permanently fluorescent Pyro-PL are imaged with the CRI Maestro System, and the resulting images resolved into probe and autofluorescence on the basis of emission spectrum deconvolution. These images confirm that Pyro-PL localizes in the tumor within minutes, and persists for about 3 hours, consistent with FIGS. 12A and 13A. By 2 hours, the probe is also being removed from circulation, with concentration first in the liver, and then in the intestine for excretion in the stool. FIG. 12 confirms this result, where organs removed from Pyro-PL containing mice were imaged ex vivo on the IVIS System at 24 h. At 2 h, the majority of the fluorescence appears in the liver (not shown), and at 24 h, major fluorescence persisted in the liver, kidney and digestive tract. These data form the basis for pharmacokinetic studies using fluorolabeled probes.

Example 7: Modeling Fluorophore Activation In Vivo

A mathematical formulation was developed to model fluorophore activation in vivo. This is based on a one-compartment pharmacokinetic model that takes into account both probe wash-in and wash-out as well as probe activation. First the data from Pyro-PL pharmacokinetics were fit followed by extraction of activation constants for Pyro-PL-BHQ. First the Pyro-PL tumor:muscle ratios concentration versus time profiles were fit to the equation:

$$C_i = C_0 \frac{k_a}{k_a - k}[\exp(-kt) - \exp(-k_a t)] \quad (1)$$

where $C_o$, is the observed maximum concentration, ka and k are the accumulation and elimination rate constants, respectively. Assuming that Pyro-PL-BHQ tumor fluorescence can be described by a combination of Pyro-PL pharmacokinetics and the enzymatic activation by PC-PLC, the time-dependent fluorescence can be fit to a model accounting for both of these actions:

$$R(t) = \left[C_0 \frac{k_a}{k_a - k}(\exp(-kt) - \exp(-k_a t))\right] + [[E](1 - \exp(-[A]k_e t))] + 1 \quad (2)$$

Figure 13:
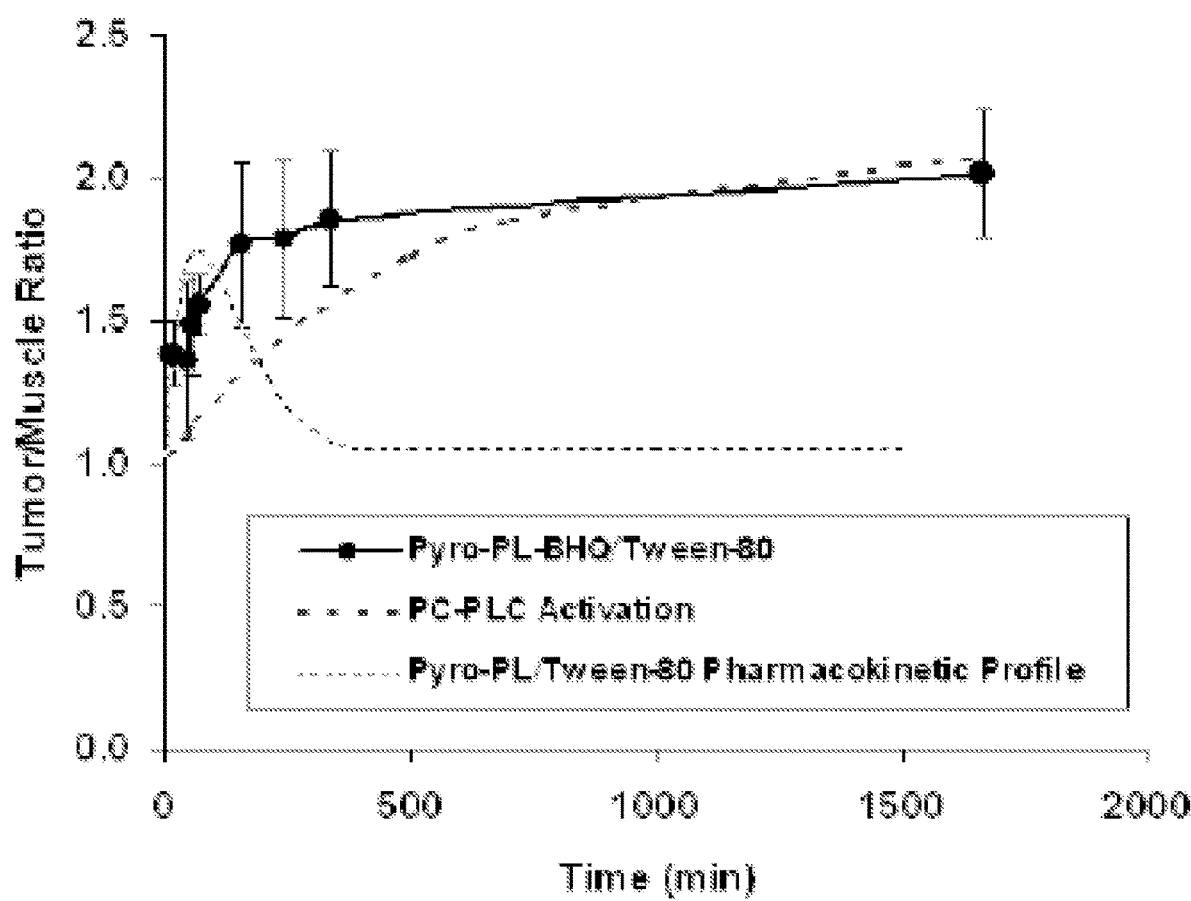
FIG. 13 shows modeling of in vivo activation of Pyro-PL-BHQ. Tumor:muscle fluorescence ratio was fit to a model accounting for Pyro-PL pharmacokinetics and enzyme activity. The pharmacokinetic profile of Pyro-PL was fit to Eqn 1 of Example 7 and subtracted from the Pyro-PL-BHQ tumor/muscle ratio to estimate the fluorescence occurring from enzymatic activation of the probe.

The enzymatic reaction is assumed to be a bimolecular second order reaction, where R is the tumor/muscle ratio, [E] is the enzyme concentration, $k_e$ is the enzymatic rate constant. The probe concentration, [Pyro-PLBHQ], is represented by [A] and is assumed to be in large excess ([A]>>[E]). FIG. 13 shows the experimental Pyro-PL-BHQ tumor:muscle ratios, the fit to the Pyro-PL pharmacokinetics, and the residual curve describing enzymatic activation of Pyro-PL-BHQ, where a $k_{obs} = k_e*[A] = 2.16 \times 10^{-3}$ sec$^{-1}$ was calculated. The phamacokinetic data provided by dual optical-radiotracer studies studies was used to validate this model. These studies are used to determine whether the assumption of whether Pyro-PL pharmacokinetics is valid, and provide information on blood and urine probe levels that is used to expand this formulation to a two-compartment model.

Example 8: Design and Chiral Synthesis of Lipid-Based Self-Quenching Fluorophores Containing a Stable NIR Fluorophore, Coupled to a Quencher Via Appropriate Linkers The preliminary data indicates that near-infrared molecular beacons sensitive to the actions of phospholipases can be synthesized via more than one route. This approach is superior to previous attempts, as the newly developed chiral syntheses provides delivery of 100% compound that is sensitive to enzymatic attack, and doubling the potential signal to noise over racemic mixtures. Starting from enantiopure Lyso-PE (Avanti Polar Lipids, Inc., Alabaster, Ala., USA) and sn-glycero-3-phosphocholine (Bachem, Switzerland) optically pure Pyro-PL-BHQ and PyroPyro-PtdCho was synthesized according to (Scheme 1). Two NIRF molecules attached to the sn-1 and sn-2, positions respectively, quench each other and released by the action of PLA1/PLA2. A prototype molecule was synthesized (PyroPyro-PL) and the effect of spacers on sensitivity to PLA2 activity of this self-quenching fluorophore is examined.

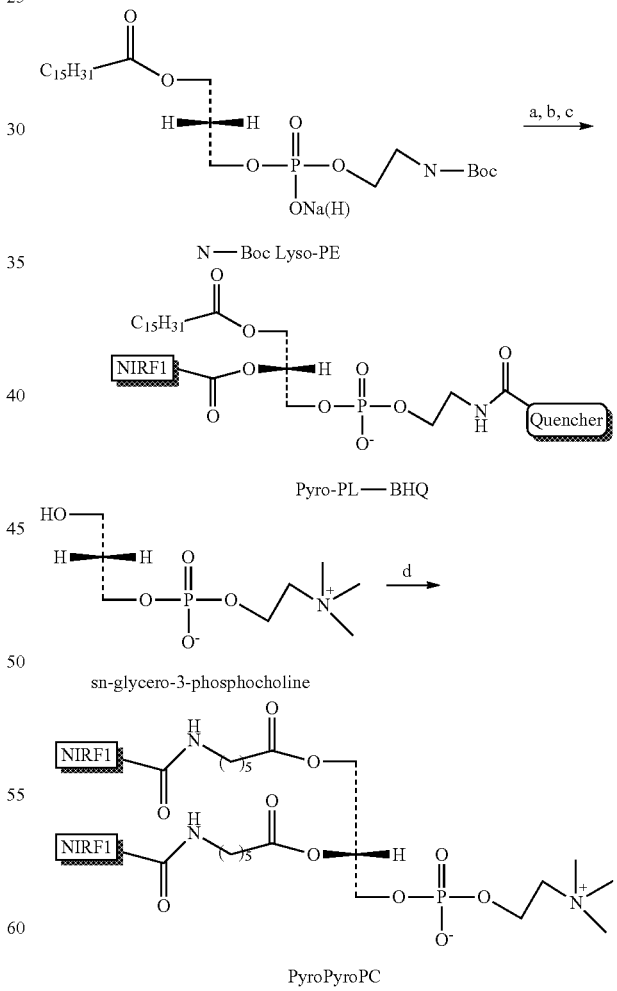

Scheme 1. Synthesis of chiral NIRF1-PL-Quencher and NIRF1NIRF1-PL (NIRF1 = Pyro)

a) Pyro acid, EDC, DMAP, CH$_2$Cl$_2$, Ar, dark, r.t., 72 h; b) TFA, CH$_2$Cl$_2$, 0° C., Ar, dark, 4 h; c) QuencherCO$_2$—NHS, Et$_3$N, CH$_2$Cl$_2$, r.t., dark, 12 h; d) EDC, DMAP, CH$_2$Cl$_2$, Ar, dark, 40° C.; 72 h.

The fact that there is no racemization during a "basic" coupling is a major advantage. Advanced syntheses of new optically pure probes are being performed (Scheme 2). Optically active phospholipids and their analogs possessing natural chirality (enantiomeric excess, ee=98-99%) can be easily synthesized de novo starting from (S)-glycidol and/or its derivatives (e.g. paratoluenesulfonate, tosylate, OTs). Optically pure (S)-glycidol and (R)-glycidol as well as their tosylates are available in large scale from Bosche Scientific, New Brunswick, N.J., USA). That is why most syntheses are designed using these products as precursors of chiral glyceryl moieties. Notably, any of compounds described could also be produced using enantiopure-starting materials isolated from natural products, such as Lyso-PE and sn-glycero-3-phosphocholine.

In order to investigate biochemical processes in tumor cells and in vivo, the structure and physical properties of target near-infrared phospholipid probes have to be as close as possible to the natural analogs (size, polarity, chirality, lipophilicity, steric hindrance, etc). Since there are relatively few neutral NIRFs, the non-polar porphyrin NIRFs were incorporated into the lipophilic sn-1 and sn-2 portions of the molecules, whereas positively charged BHQ-quenchers are attached to a nitrogen atom in the polar head group of PtdEtn. The prototype phospholipid probe Pyro-PL-BHQ showed a remarkable specificity for PC-PLC. The distance between the active site of the enzyme and the bulky NIRF-Quencher pair would influence phospholipase activity because of steric hindrance. Different linkers (spacers) have been incorporated between the NIRF and sn-1, 2 on the glycerol backbone, as well as between the phosphorus atom on the head group and the quencher. The effects of increasing these spacer distances on enzyme specificity are tested in, and the optimal spacers for each phospholipase isoform determined.

The phospholipase-sensitive fluorescent probes that can distinguish phospholipase type and/or isoform and differentiate their activities are developed. For this purpose special "discriminating" phospholipid-like NIRF-bearing molecules, that are "invisible" for the appropriate lipases, are designed. Such discrimination could be achieved by replacing the acyl with an alkyl at the sn-1 or sn-2 positions (i.e. incorporation of ether bonds instead of ester bonds), thus eliminating the sensitivity to PLA1/PLA2/LysoPLs (Scheme 2).

Alternatively, displacing of either bridging oxygen atoms at the phosphorus by NH, NR, S, CH2, CF2 etc. renders the product insensitive to PLC or PLD. A third possibility is changing the chirality at the sn-2 carbon and incorporating chirality at the phosphorus atom by alkylation of the non-bridging oxygen atom. In the first two steps of Scheme 2 (a and b) the two chlorine atoms of methyl dichlorophosphite (MeOPCl$_2$) are replaced subsequently with optically active S-glycidoxyl and N-Boc protected NH$_2$(CH$_2$)$_n$O—, n=2, 4, 8, 12, 16 by reactions of the corresponding alcohols (S-glycidol and Boc-NH (CH$_2$)$_n$OH) in the presence of triethyl amine (TEA). The thus obtained trialkyl phosphite is oxidized into the phosphate by tert-butyl peroxide tBuOOH (step c). Next, the cleavage of the oxirane ring by C$_{15}$H$_{31}$CO$_2$H/C$_{15}$H$_{31}$CO$_2$Cs in DMF leads to the R-Lyso-derivative (step d), which in turn is coupled with NIRF-COOH or the spaced NIRF-CONH—(CH$_2$)$_m$CO$_2$H (m=5, 11, 17) in the presence of N-(3-dimethylaminopropyl)-N'-ethyl carbodiimide hydrochloride (EDC) and 4-dimethylaminopyridine (DMAP) in CH$_2$Cl$_2$ (step e). The spaced NIRFs are used for phosphatidylethanolamine (PtdEtn) derivatives (with the quencher held at n=2). The following step f is N-Boc- and PO-Me-deprotection under the action of trifluoroacetic acid (TFA) and triethylsilane (TES) in CH$_2$Cl2. The final coupling with quencher-CO$_2$—NHS (step g) results in the target PLA2/PLC/PLD-activable probes.

Example 9: Structure Function Studies: Synthesis of General Phospholipid Probes Potentially Sensitive to all Phospholipases Optimization of spacer lengths NIRF-sn-2 and PO-Quencher: A general phospholipase-sensitive probe is synthesized by incorporating the NIRF into the sn-2 portion and the quencher at the nitrogen atom of the polar head group. The sn-1 portion contains a paraffinic acyl (usually palmitoyl C$_{15}$H$_{31}$CO). To investigate structure-activity correlations and optimize probe structure with the highest activity related to different PLs, spacers are incorporated between the NIRF and the sn-2 glycerol carbon or between the phosphorous atom of the head group and the BHQ quencher. For the NIRF separation, ω-aminocarboxylic acid spacers (NH$_2$(CH$_2$)$_m$CO$_2$H, m=5, 11, 17), are used whereas ω-aminoalcohols are used to separate the quencher from the head group. (NH$_2$(CH$_2$)$_n$OH, n=4, 8, 12, 16). Thus a minimum of 8 PLA2/PLC/PLD activated probes are synthesized. The synthesis is designed to obtain high yields at each step and facilitate isolation of the intermediates. To do this only non-polar compounds are used, with polarity being introduced only at the last step.

Example 10: Structure Function Studies: Synthesis of Phospholipid Probes Insensitive to PLA2

Having found the PtdEtn-derivative with optimal sensitivity to PLA2/PLC/PLD (k=1, m opt, n=2, Scheme 2, a-g), a probe insensitive to PLA2 is designed in order to investigate the activity of PLC and PLD (Scheme 2, k-m).

Scheme 2. Synthesis PLA2/PLAC/PLD and PLC/PLD activated probes.

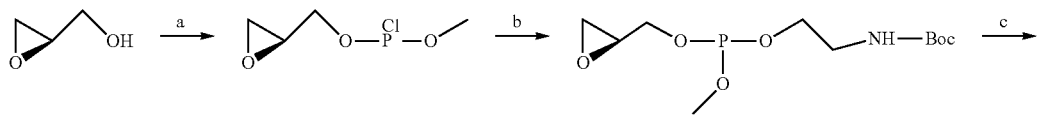

-continued

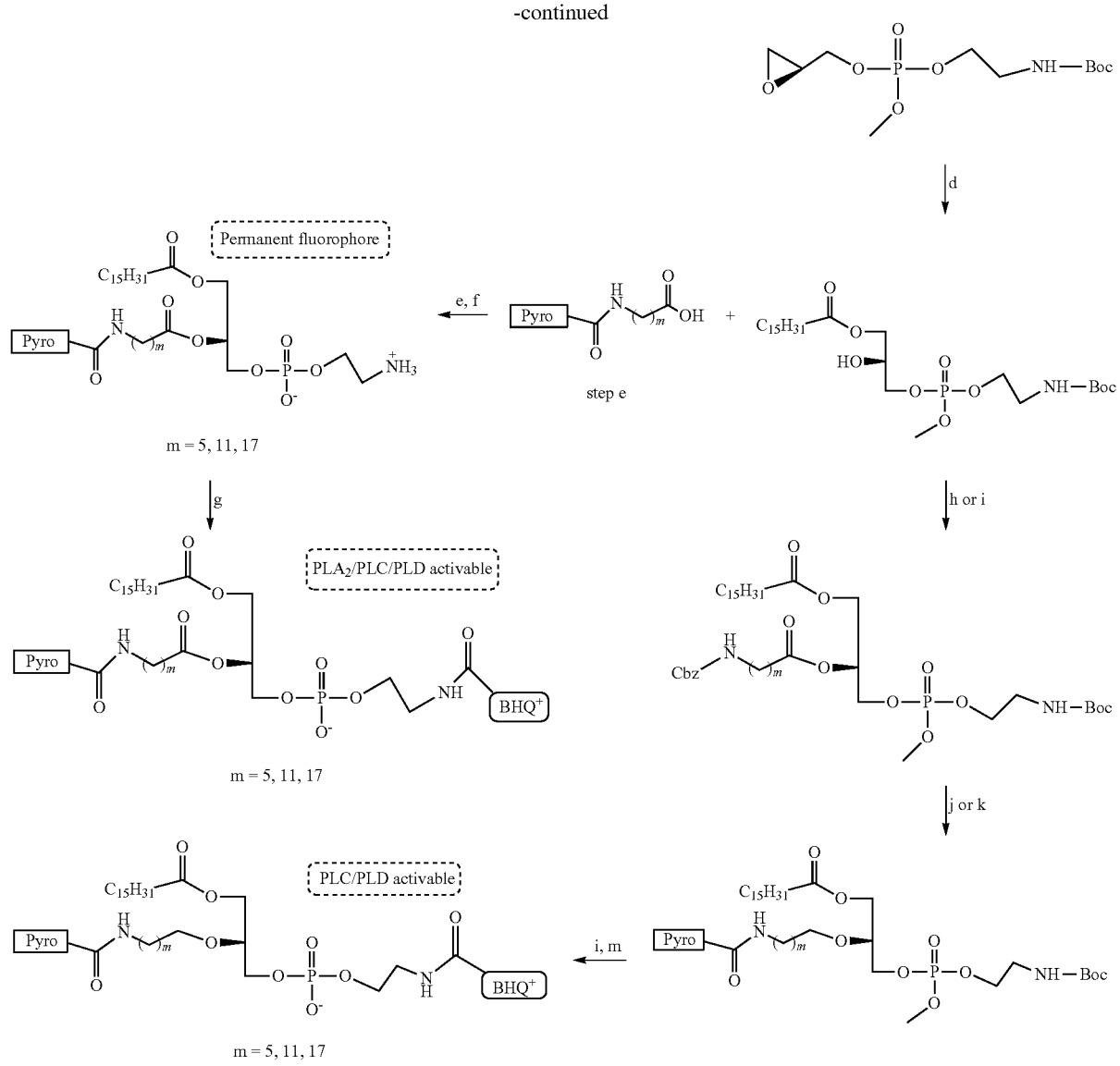

a) MeOPCl$_2$, TEA, CH$_2$Cl$_2$; b) Boc—NH(CH$_2$)$_n$OH, TEA, CH$_2$Cl$_2$; c) tBuOOH, CH$_2$Cl$_2$; d) C$_{15}$H$_{31}$CO$_2$Cs, C$_{15}$H$_{31}$CO$_2$H, DMF; e) EDC, DMAP, CH$_2$Cl$_2$; f) TFA, TES, CH$_2$Cl$_2$; g) Quencher-COO—NHS, Py, CH$_2$Cl$_2$; h) Cbz—NH(CH$_2$)$_m$CH$_2$OC(=NH)CCl$_3$, Tf—TMS; CH$_2$Cl$_2$;
i) Cbz—NH(CH$_2$)$_m$CH$_2$OTf, NaH, DMF; j) H$_2$, Pd/C,
EtOH; k) Py, CH$_2$Cl$_2$; l) TFA, TES, CH$_2$Cl$_2$; m) Quencher-COO—NHS, CH$_2$Cl$_2$, Py The product of step d in Scheme 2 is used as a starting material using the protected ethanolamine derivative with n=2. An sn-2 ether derivative is chosen to replace the corresponding sn-2 ester for this probe, since this bond is stable to esterase-mediated hydrolysis at the sn-2 position and have a similar structure. For the spacer between the sn-2 carbon atom and the NIRF, ω-aminoalcohols H2N(CH$_2$)$_m$ optCH2OH that have the same number of carbon atoms as the corresponding spacer w-aminocarboxylic acid (Scheme 2 steps e-g) are employed. Then benzyloxycarbonyl (BnOCO, Cbz) protected ω-aminoalcohol Cbz-NH(CH$_2$) m$_{opt}$ CH$_2$OH is coupled to the sn-2 COH derivative (steps h or i). In step h Cbz-NH(CH$_2$)$_m$CH$_2$OC(=NH)CCl$_3$ (the adduct of the alcohol and CCl3CN) in the presence of trimethylsilyl triflate (Tf-TMS) in CH$_2$Cl$_2$ is used. For step i sodium hydride NaH and triflic ester of the alcohol in DMF is taken. The final choice between steps h and i depends on m opt. For m opt=5 method h is preferable, while for m opt=11, 17 the method I is used. The next step j represents a selective deprotection of the Cbz-protected amino group in the sn-2 portion. This selective cleavage is catalytic hydrogenation in MeOH in the presence of Pd on charcoal. The thus obtained amine is coupled with N-hydroxysuccinimide derivative of NIRF (NIRF-CO$_2$—NHS) in CH$_2$Cl$_2$ in the presence of Py (step k). A TFA-TES cleavage of N-Boc and PO-Me release NH$_2$ and POH groups, correspondingly (step 1). In the last step m, this NIRF-containing PtdEtn is coupled with quencher —CO2-NHS in CH2Cl2 in the presence of Py giving in result target PLC/PLD activatable phospholipid probe with the optimal distance between NIRF and the sn-2 atom.

Example 11: Structure Function Studies: Synthesis of Phospholipid Probes Insensitive to PLD Knowing the optimal distance between the sn-2 glycerol carbon and the NIRF, a phospholipid NIRF-containing probe in the sn-2 portion insensitive to PLD is synthesized. As in the all above structures a nonsubstituted palmitoyl moiety is placed at the sn-1 position. To discriminate PLD 2-aminoethoxy group on the head group is displaced with a 3-aminopropyl group. In other words, the polar head group contains 3-aminopropyl phosphonate, a compound containing a carbon-phosphorus bond (P—C), thus preventing PLD-catalyzed hydrolysis.

Two possible synthetic approaches are demonstrated in Scheme 3.

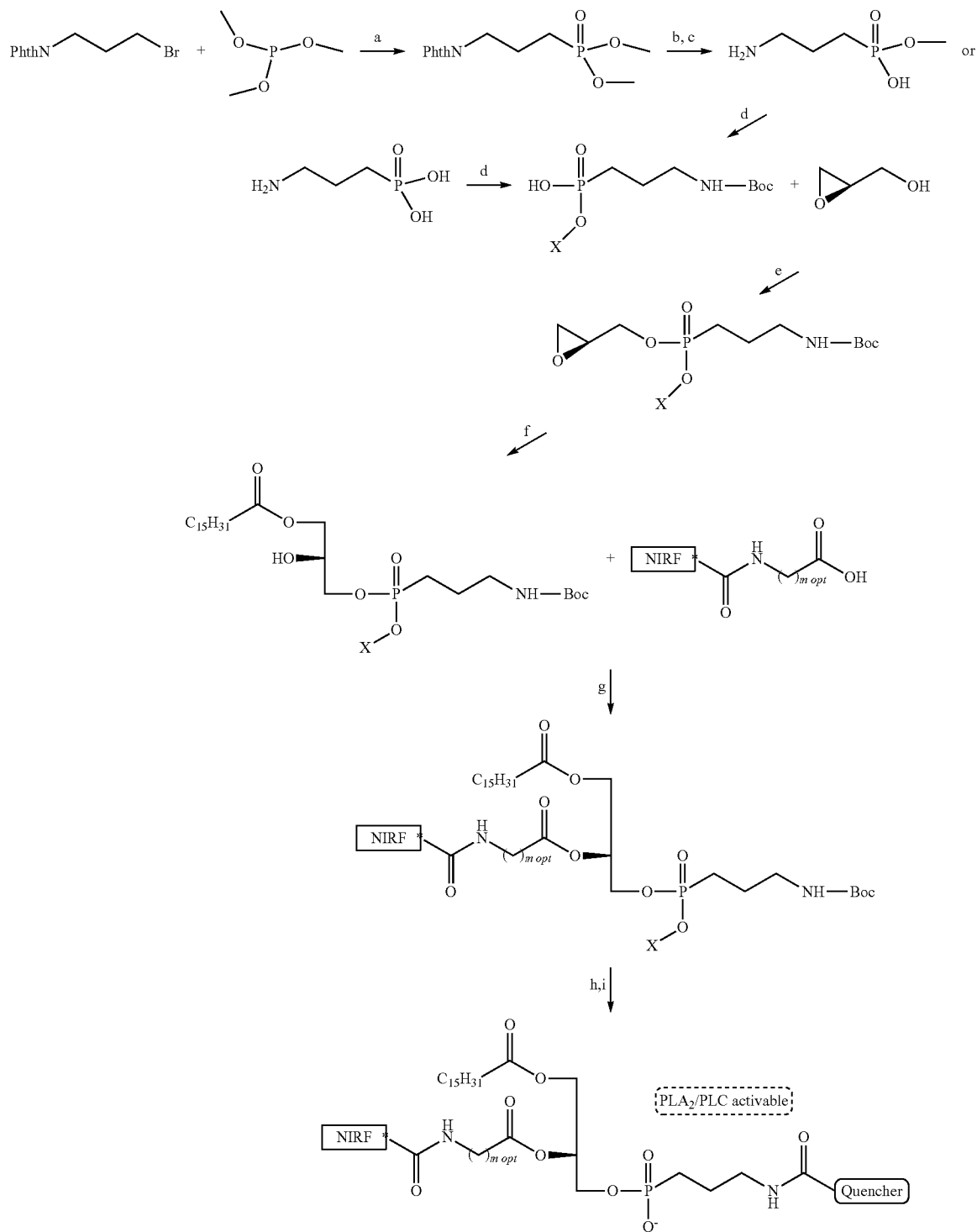

Scheme 3. Synthesis PLA2/PLC activated probes.

X = H, CH₃
a) reflux, Ar;
b) NaOH, H₂O;
c) N₂H₄·H₂O, CH₂Cl₂;
d) Boc₂O, 1,4-dioxane, H₂O, NaOH;
e) TPSNT, Py, CH₂Cl₂;
f) C₁₅H₃₁CO₂H, C₁₅H₃₁CO₂Cs, DMF;
g) EDC, DMAP, CH₂Cl₂;
h) TFA, TES, CH₂Cl₂;
i) QuencherCO₂—NHS, Py, CH₂Cl₂

The first approach is Scheme 3 steps a-h, X=Me. The second one is steps d-h, where X=H. The last step i is the same for both. The compounds involved in the first pathway are less polar due to the protection of POH by the Me group and thus easier to isolate by chromatography. The second approach includes polar substances, which are harder to isolate. Nevertheless the second pathway consists of only 6 steps in comparison with the 9 steps in the first one. In the first synthetic pathway the initial step a is a neat Arbuzov reaction between 3-phtalimido-1-propyl bromide (PhthN(CH₂)₃Br and trimethyl phosphate which results in the dimethyl ester of 3-phtalimido-1-propyl phosphonic acid (PhthN(CH₂)₃P(O)(OMe)₂). The step b is a partial basic hydrolysis in water that leads to methyl ester of 3-phtalimido-1-propyl phosphonic acid (PhthN(CH₂)₃P(O)(OMe)(OH)). Hydrazine hydrate (N₂H₄.H₂O) in CH₂Cl₂ is used to deprotect the amino group in the next step c. However this amino group has to be protected by a base insensitive protecting group until the last step. That is why a Boc-protection is undertaken in step d by treatment with Boc₂O in 1,4-dioxane-water-NaOH. The same reaction d is the first step for the second pathway, namely, Boc-protection of commercially available 3-amino-propyl phosphonic acid in THF-water-NaOH (pH~9). Starting from step d the both syntheses are the same, varying in such details as solvent amount and isolation methods for intermediate products. The coupling of POH derivatives with S-glycidol (step e) occurs with triisopropylphenyl sulfonyl 3-nitrotriazol (TPSNT) in CH₂Cl₂ in the presence of Py. Such a coupling produces phosphorylated R-glycidyls. The cleavage of the oxirane ring by $C_{15}H_{31}CO_2H/C15H31CO2Cs$ in DMF (step f) produces the Lyso-like analogs. A NIRF with the previously attached optimal spacer (NIRF-CONH(CH₂)m$_{opt}$ CO₂H) is conjugated with these Lyso-analogs by the action of EDC, DMAP in CH₂Cl₂. The following TFA/TSE mediated de-protection in CH₂Cl₂ (N-Boc cleavage for both X=H, Me; and PO-Me cleavage for the Me-substituted phosphate (X=Me) produces NIRF-containing 1,2-diacyl glyceryl ester of 3-amino-1-propyl phosphonic acid (step h). The latter is treated with quencher —CO₂—NHS in CH₂Cl₂ in the presence of Py resulting in the target PLD discriminating phospholipid probe.

Example 12: Structure Function Studies: Synthesis of Phospholipid Probes with the Optimal Spacer in the Sn-2 Portion that are Insensitive to PLC The design of PLC-discriminating phospholipid probes can take many different forms. The oxygen atom bridging the glyceryl and phosphorus moieties could be displaced by NH, NR, CH₂, CF2 or S. Synthesis begins with the synthesis of the C—NH—P derivative, because it does not change dramatically the structure and physical properties of the probe relative to the original C—O—P-compound (Scheme 2). As in the previous structures the sn-1 portion is palmitate. As the P—N bond can be sensitive to the action of strong Brönsted acids (TFA, HCl) the following synthetic pathway is designed without the use of TFA-mediated deprotection reactions (Scheme 4).

Scheme 4. Synthesis of PLA2/PLD activated probes.

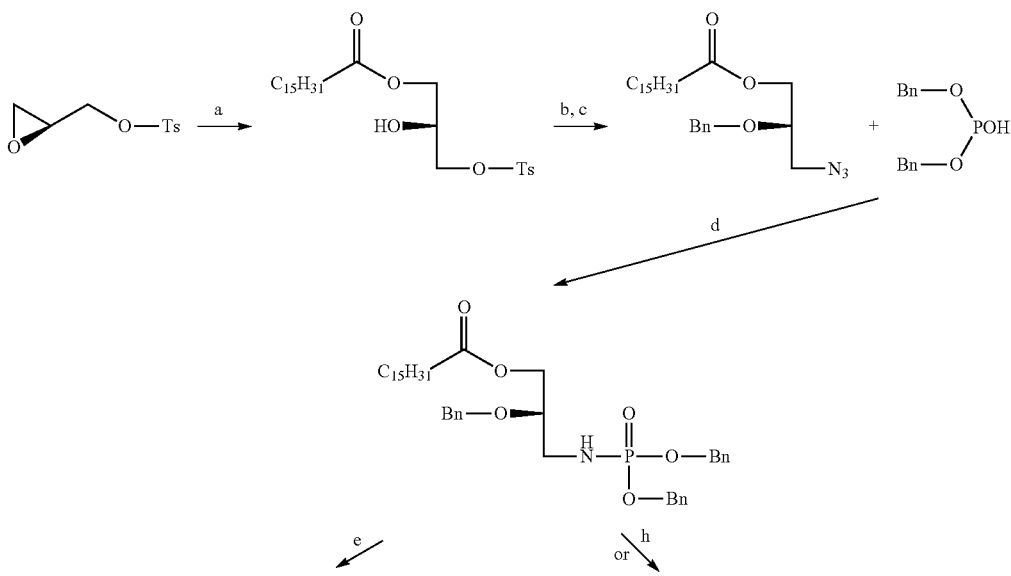

-continued

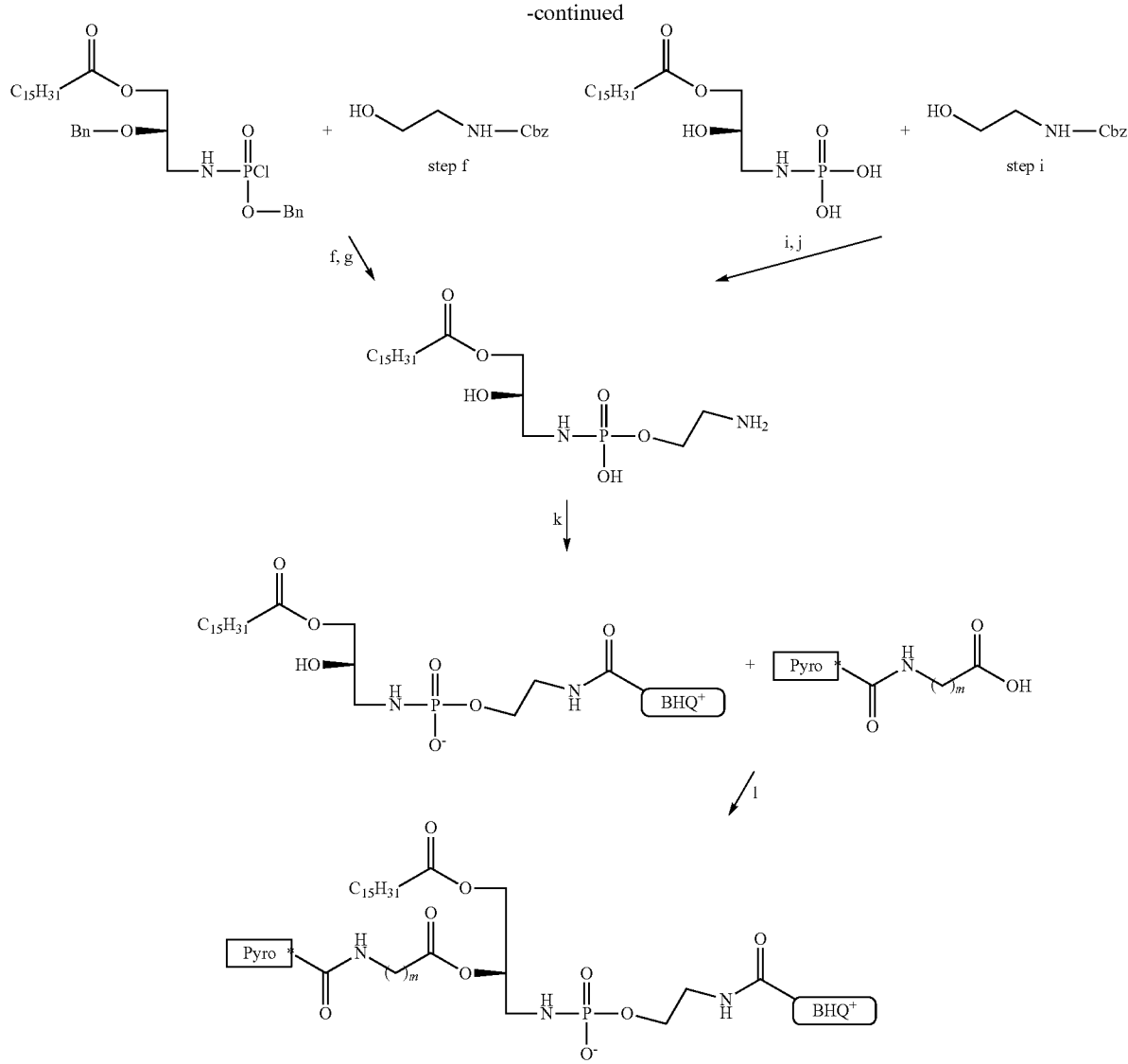

m = 5, 11, 17
a) $C_{15}H_{31}COOH$, $C_{15}H_{31}COOCs$, DMF;
b) BnO—C(=NH)CCl$_3$, Tf—TMS;
c) NaN$_3$, DMF;
d) TEA CH$_2$Cl$_2$;
e) oxalyl chloride, DMF;
f) TEA, CH$_2$Cl$_2$;
g) H$_2$, Pd/C, MeOH;
h) H$_2$, Pd/C, MeOH;
i) TPSNT, Py, CH$_2$Cl$_2$;
j) H2, Pd/C, MeOH;
k) Quencher COO—NHS, t-AmOH, Py;
l) EDC, DMAP, CH$_2$Cl$_2$ Only benzyl (Bn) and Cbz groups are used. These protecting groups can be removed by catalytic hydrogenation under neutral conditions. The starting compound for this synthesis is S-glycidyl tolylate that has been successfully used in the synthesis of optically active phospholipids. The initial step a is the cleavage of the oxirane ring by $C_{15}H_{31}CO_2H/C_{15}H_{31}CO_2Cs$ in DMF. To avoid the possible formation of phosphorus-containing cyclic byproducts the sn-2-COH group is protected by Bn under the action of benzyltrichloroacetimidate (Bn-OC(=NH)CCl$_3$) in CH$_2$Cl$_2$ in the presence of trimethylsilyl triflate (Tf-TMS) (step b). Then a tosylate moiety is replaced with azidogroup by the reaction c with sodium azide (NaN$_3$) in DMF. The addition of a phosphorus moiety is carried out by the use of an elegant, smooth Staudinger-like reaction. In this step d the alkyl azide is reacted with dibenzyl phosphite in CH$_2$Cl$_2$ in the presence of catalytic amount of triethyl amine (TEA) resulting in an N-alkyl phosphamide There are two possibilities for the further synthesis: first is reactions e-g, second one is represented by steps h-j. In step e one Bn-O group at the phosphorus is replaced by a chlorine atom. The chlorination agent is oxalyl chloride in the presence of catalytic amount of DMF. Thus obtained P—Cl derivative is coupled in step f with Cbz-N protected ethanolamine in $CH_2Cl_2$ with the use of TEA as a base. The following catalytic hydrogenation h deprotects COH, POH and $NH_2$ groups. An alternative route can be debenzylation by catalytic hydrogenation on Pd/C in MeOH (step h) followed by a coupling of the substituted N-glycerylamidophosphoric acid with Cbz-$NHCH_2CH_2OH$ in $CH_2Cl_2$ in the presence of TPSNT and Py (step i), and one more hydrogenation on Pd/C in MeOH to release the terminal amino group (step j) and give rise to an "aza-Lyso-PE".

A selective acylation of the terminal amino group (step k) is undertaken by quencher —$CO_2$—NHS in such a weak nucleophilic alcohol as tert-Amyl alcohol (tAmOH) in the presence of Py. The final step l is O-acylation of the sn-2-COH by the NIRF-C(O)N($CH_2$) $m_{opt}$ $CO_2H$ in $CH_2Cl_2$ by EDC/DMAP. The thus obtained probe can be activated by PLA2 and PLD.

Example 13: Structure Function Studies: Synthesis of Bis-NIRF-Bearing PtdCho Probes with Varying Spacers in the Sn-1 and Sn-2 Portions Sensitive to PLA2 Only In a preliminary study, it was demonstrated that two Pyro moieties can quench each other through fluorescence resonance energy transfer. This quenching is less efficient than the quenching by a dark quencher such as BHQ. Nevertheless, such self-quenching or similar-quenching is also applied in optical imaging, when the use of polar charged quenchers is undesirable. PtdCho analog near infrared probes were designed where two equal NIRFacyls are attached to sn-1 and sn-2 positions (Scheme 5).

Scheme 5. Synthesis PLA1/PLA2 activated probes.

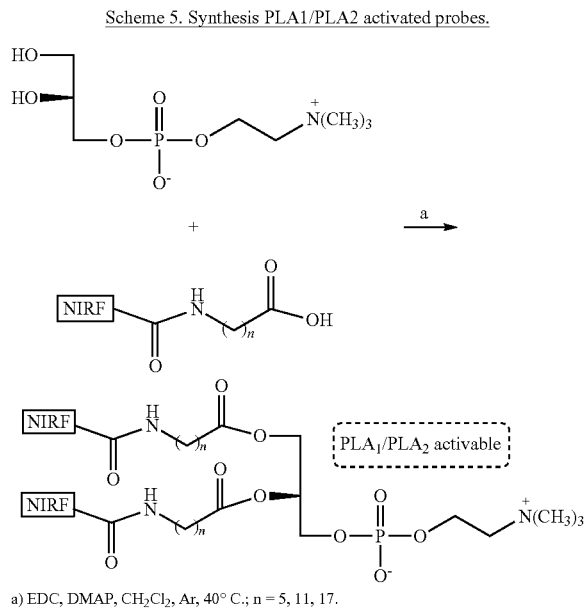

a) EDC, DMAP, $CH_2Cl_2$, Ar, 40° C.; n = 5, 11, 17.

Linkers of different length separate the NIRF moieties and glycerol backbone. They are ω-amino acids (caproic, dodecane and octadecane carbonic acids). Varying spacer lengths are designed to find an optimal structure with maximal difference between final (after cleavage) and initial (before cleavage) fluorescence. These compounds are the only derivatives of choline. The test results for PC- and PE- derivatives are used to compare phospholipases activity relative to these two head groups.

Due to poor solubility in non-water media the starting sn-glycero-3-phosphocholine (GPC) is usually used in complex with toxic cadmium chloride ($CdCl_2$). To avoid possible contamination of phospholipid probes with cadmium derivatives the original reaction of sn-glycero-3-phosphocholine with NIRF carbonic acids (the spacer was 6-aminocaproic acid, n=5) in $CH_2Cl_2$ under Ar in the presence EDC and DMP was developed, raising the reaction temperature up to 40° C. (step). After several days the target product, PyroPyro-PL, was obtained with reasonable yields (15-30%) relative to GPC. With increase of n from 5 to 11 and 17 bisNIRF probes are obtained with the lipophilic alkylidene moieties similar to the natural PCs.

As the result of the chemical studies described above, convenient high yield syntheses for the chiral near infrared phospholipid probes selective for the specific phospholipases is developed. The three prototype compounds have provided the basic synthetic pathways required for all the syntheses, which yields the majority of the compounds. One major advance in these protocols was the synthesis of the chiral starting materials for all the protocols directly, rather than relying on relatively expensive biological starting materials (e.g. Lyso-PtdEtn).

Example 14: Demonstration that the Self-Quenching NIR Fluorophore Probes can be Activated by the Enzymatic Action of Phospholipases Prior to administration in vivo, the probes are subjected to rigorous in vitro testing to determine activity and specificity. This includes initial assessment of in vitro reactivity with commercially available phospholipases, followed by determination of specificity and sensitivity to particular phospholipase types and isoforms. For candidate probes that display sensitivity to a particular phospholipase or group of phospholipase, a detailed kinetic analysis is performed. These probes are then tested in cell experiments. Important aspects of cellular testing include methods of delivery, in situ localization and activation, and assessment of toxicity.

Liposome Formulation and Critical Concentrations:

Critical to all imaging experiments is not only signal to noise but also contrast to noise. The use of high efficiency dark BHQ or BBQ quenchers, and fluorophores that emit in the NIR frequencies allow a high degree of contrast to noise to be achieved. First, the degree of quenching is assessed by measuring the absorption and fluorescence emission spectra of the synthesized probes and comparing them with the native fluorophore, or with the corresponding fluorescent analogs synthesized without quencher, as was shown in FIG. 6. Since absorption as well as emission frequency can depend on local environment, including hydrophobicity, it is important to perform these measurements in organic solvent, as well as in liposome formulations. Since these experiments are non destructive and can be performed using minute amounts of fluorophore, they can be performed as the initial stage of another experiment.

The next step is to incorporate the fluorophores into liposomes. Three standard formulations for Liposomes are proposed: pure PtdCho, PtdCho:PtdEtn:Chol (2:1:1) and PtdCho:Sph:PtdGro:Chol (5:5:1:2). These formulations are increasingly complex and are designed to approximate plasma membrane lipid formulations. The MF of the phospholipase-activated fluorophores is kept relatively low in these formulations (0.005-0.5 mole %). This prevents phase separation of the fluorophores and minimizes intermolecular interactions that lead to additional fluorophore quenching. Since detection sensitivity is at the pico-nano molar range in the fluorescent plate reader, this is not a problem. Injections as little as 50 ng can be detected in animal models. Once liposome formulation is achieved, optimal liposomal concentrations of the fluorophores need to be determined to estimate the degree of intramolecular quenching by fluorophore stacking and intermolecular quenching of released fluorophore by unreacted quenched molecules. Preliminary data from this type of experiments were described in FIG. 14. These experiments, which are necessary for accurate determination of fluorophore kinetics, utilize liposomes containing the permanently fluorescent analogs in combination with the quenched molecules. The experiments described are performed in 96-well plates and fluorescence measured using a fluorescent plate reader. In the first set of experiments, the degree of intramolecular quenching is assessed by varying the relative MF of fluorophore to lipid while keeping the total fluorophore concentration constant. A deviation from linearity in fluorescence emission at higher fluorophore MF indicates the aggregation of Pyro molecules due to stacking of the planar molecules. This determines the maximum mole fraction of Pyro-labeled phospholipids that can be incorporated into liposomes with no aggregation or phase separation. Once this value is established, the second set of experiments can be performed in which the linear increase in fluorescence associated with increased fluorophore concentration is compared to the reduced fluorescence values obtained from mixtures of permanently fluorescent and self quenched molecules at the same total fluorophore concentration. The reduction in fluorescence observed arises from intermolecular quenching of the fluorophore by adjacent molecules containing BHQ3 quencher head groups. From these data, a correction factor can be calculated and calibration curves constructed to more precisely estimate the true fluorophore concentration, and thus determine the absolute enzyme substrate conversion rate in the experiments described in the following section.

Determining Enzyme Specificity and Sensitivity: Following the completion of these preliminary experiments, the sensitivity and specificity to enzyme isoform can be determined for each of the phospholipase-activated fluorophores. Relative sensitivity is estimated by monitoring the time-dependent release of Pyrofluorescence following the addition of enzyme to liposomes containing a phospholipase-activated probe. For each probe, a bank of phospholipases is tested that includes recombinant human sPLA2-IB, IIA, IID, IIE, V, X and XII, type IA sPLA2 (*naja mossambica mossambica*), type IB sPLA2 (porcine pancreas), broad spectrum and PtdCho-specific PLD (*S. chromofuscus*) PC-PLC, PI-PLC and SMase (*B. cereus*). For each enzyme type or isoform, the liposomes is reconstituted using buffers, pH and temperature conditions that are ideal for each enzyme. These assays are performed in quadruplicate in 96-well plates and assessed using a fluorescent plate reader. Relative sensitivity is calculated as the ratio of initial rate of fluorophore release compared to control wells to which only buffer has been added. Enzyme specificity is assessed using TLC and HPLC-MALDI-TOF mass spectrometry. In most cases, it is possible to isolate sufficient products for TLC and MALDI-TOF from the 96 well plates by extraction with chloroform:methanol, followed drying under dry nitrogen gas and resuspension in solvent. From TLC a quick and inexpensive estimate of specificity can be obtained—Pyro, BHQ3, and the quenched Pyro-PL-BHQ have different absorption maxima and can be distinguished easily by the naked eye based on their color. This distinction is enhanced by viewing the TLC plates under near-UV light (385 nm). On the basis of color, degree of migration and comparison with standards, a reasonable estimate of activity and of cleavage specificity can be determined. These data can be confirmed by the use of HPLC MALDI-TOF. The amounts of substrates produced and remaining reactant can be estimated from the relative areas under HPLC peaks, and the identities of these compounds can be confirmed by molecular weights obtained from MALDI-TOF mass spec.

Kinetic Analysis:

From the data produced above, probes that display sensitivity for an enzyme type or isoform are selected for detailed kinetic analysis. Since structure-function correlations are performed by synthesizing a number of fluorophores that vary in chain length and linking groups, the kinetic analysis produces valuable data on the relative sensitivity of these probes to their target enzymes. This kinetic analysis follows a standard protocol, and all assays are performed in 96-well plates and read on the fluorescent plate reader. First the optimal enzyme concentration is determined by measuring fluorescence release as a function of units of added enzyme. Usually a range of 0.1-3 units is sufficient to determine the range where the activity is linearly proportional to enzyme concentration. Further experiments are then performed as a function of substrate concentration using an enzyme concentration that is in the linear regime. From this data, a Michaelis-Menten analysis is performed by plotting initial rate of substrate formation (Vo) as a function of substrate concentration [S]. The parameters—1/Km and 1/Vmax can be determined from the slope and y intercept of linear double inverse Lineweaver-Burke plot of 1/Vo vs 1/[S] (FIG. 3).

Surface-dilution Michaelis-Menten kinetics: Surface dilution kinetics are used to best describe the actions of enzymes at interfaces. They involve two steps, a bulk step, where the enzyme reversibly docks with the surface and a surface step, where catalysis occurs.

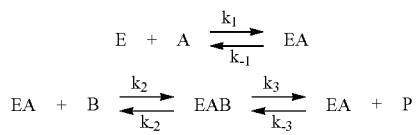

The bulk step involves the docking of the soluble enzyme (E) with the surface (A) to form an enzyme-liposome complex (EA). This step is a function of the bulk concentrations of E and A. The surface step involves the binding of the EA complex to a specific lipid molecule, B, forming an EAB complex, followed by catalysis to form product P and regenerating the EAB complex. This process allows the separation of the effects of bulk docking, which is constant for a constant amphiphile concentration, from the catalytic process. The kinetic equation for the surface dilution scheme is given by:

$$V = \frac{V_{max}[A][B]}{K_s^A K_m^B + K_m^B + [A][B]}$$

where $K_s^A = k-1/k1$ and $K_m^B = (k-2+k3)/k2$. Vmax is the true Vmax at infinite bulk concentration of phospholipid substrate, $K_m^B$ is the interfacial Michaelis constant and $K_m^B$ is the dissociation constant. Experimentally, this problem is solved by successively diluting catalytically active substrate B (e.g. PtdCho and Pyro-PL-BHQ) in the presence of an inert micelle-forming compound, such as Triton-X100, and measuring initial reaction rate, $V_0$, as before. A standard Lineweaver-Burke graph is constructed as a plot of $1/V_0$ as a function of $1/[B]$. A plot of the V intercepts of these plots as a function of $1/[B]$ yields a linear plot with a y intercept of $1/V$max and an x intercept of $K_m^B$ A plot of the slopes of the Lineweaver Burke graphs as a function $1/[B]$ yields a linear plot with a y intercept of 0 and an x intercept of $K_s^A$ $K_m^B/V$max. Each synthesized fluorophore is thus diluted in PtdCho liposomes at with increasing concentrations of Triton X-100 and the surface dilution kinetic parameters measured accordingly.

Demonstration that the self-quenching NIR fluorophore probes can be delivered to cultured cancer cell lines and activated in situ by treatment with anticancer drugs leading to increased NIR fluorescence: The use of cultured cells allows initial assessment of toxicity, optimization of delivery vehicles, the determination of which cell types takes up and activates the probes and which drug treatments leads to an in situ activation. In addition, inhibition studies are performed to further characterize intracellular activation, which in combination with extraction and characterization of products allow a detailed assessment of phospholipase activity. Quantitative assessment of fluorescence release is done using fluorimetry and flow cytometry along with qualitative information from fluorescence confocal microscopy to assess the in situ kinetics, specificity and sub cellular location of probe accumulation and activation (FIG. 6).

Two cell lines are employed, the human prostate cell line DU145 and the human Non-Hodgkin's lymphoma cell line WSU-DLCL2. These cell lines were chosen because they have differing native levels of choline metabolites and have known responses to chemotherapeutic agents that result in changes to their choline metabolite levels. Each of the fluorophores that was tested for phospholipase specificity in enzyme assays is assessed quantitatively in vitro. The first set of experiments is to assess the level of cytotoxicity of these probes. To do this, the probes are dissolved in ethanol or constituted in liposomes and added in quadruplicate to cells in 24 well plates in a concentration-dependent fashion. The cells are treated with the fluorophore for 24 or 48 hours and toxicity assessed using the MTT assay or trypan blue exclusion. In the case that the fluorophores are toxic, caspase-3 assay or a TUNEL staining assay is used to check for apoptosis.

In vitro delivery to cultured cells. Liposomes or micelees are used to disperse the fluorescent probes. Cells seeded onto tissue culture slides are washed, overlaid with the fluorophore, and examined using fluorescence confocal microscopy. These experiments are followed by similar experiments using the phospholipase-activatable probes. Two assays are used to quantify fluorescence resulting from phospholipase activity. In the first assay, cells are harvested from tissue culture flasks, incubated with pro-fluorophore and the increase in fluorescence analyzed using a Becton Dickinson FACScalibur flow cytometer. In parallel experiments, cells are seeded into 24 or 96 well plates, overlaid with fluorophore and the increase in fluorescence monitored using the bottom-up reading option on the fluorescent plate reader. The use of a fluorimeter provides an efficient quantitative method of measuring response in multiple wells using relatively little fluorophore. In cells which display a robust activation of phospholipases as measured by increases in fluorescence, cells are treated with fluorophore in larger scales (e.g. in 150 cm$^2$ tissue culture flasks) and the resulting products isolated for characterization using MALDI-TOF, which has a sensitivity as little as 100 pmoles. In these experiments, cells are treated with fluorophore containing vesicles for 1 h, the cells extracted with CHCl$_3$:MeOH, the extracts passed over a Sephadex G100 column, and fluorescent fractions measured with HPLC and MALDI-TOF.

Once baseline conditions have been established, drug and drug-inhibitor combinations are used to modulate the levels of choline metabolites in cultured cells and observe the effects on phospholipase activation. A number of potential anticancer drugs are known to cause transient increases in GPC, including cyclophosphamide, phenylbutyrate, and tetraphenylphosphonium chloride. Increases in PC-PLC can be caused via a number of stimuli including PDGF and phorbol esters such as 12-O-tetradecanoylphorbol-13-acetate (TPA). These compounds are added to cells in culture flasks or to perfused cell cultures and their effects on choline metabolite levels measured in extracts using high resolution NMR. Conditions that cause alterations in choline metabolite levels are determined. These compounds are also tested for their ability to activate PL-sensitive fluorophores in cells, using fluorescence microscopy and fluorimetry to measure fluorescence activation.

Finally a phospholipase inhibitor strategy is employed to confirm the specific phospholipase isoforms activated in the cells. The xanthate D-609 has been used extensively as an inhibitor of PC-PLC activity, whereas U-73122 is an effective inhibitor of PI-PLC. While no truly specific inhibitors of PLA2 exist, a generally accepted combination inhibition strategy exists for the delineation of PLA2 in intact cells isoforms. Both cPLA2 and iPLA2 are potently inhibited by arachidonyl trifluoromethyl ketone (AATFMK or AACOCF3) and methyl arachidonyl fluorophosphonate (MAFP), whereas iPLA2 is irreversibly inhibited by bromoenol lactone (BEL). sPLA2 is inhibited by LY311727 or indoxam. Thus if a given response, increased tCho or GPC in MR spectra or release of fluorescence, is inhibited by MAFP and AATFMK, but not by BEL, this implicates the actions of cPLA2. If the response were inhibited by both MAFP and AATFMK and BEL, the actions of iPLA2 is implicated. Inhibition by neither would imply that other phospholipases are active, in which case an alternative inhibitor strategies is employed.

It is expected, that probes sensitive to the actions of PLA2 will be activated in cell lines that have high intrinsic levels of GPC, or under conditions where concentration increases in GPC are observed. Similarly, it is expected that cells with high native levels of PC or inducible levels of PC will be able to activate PLC sensitive probes. Deviations from these results indicate the predominance of different pathways, such as the choline-kinase pathway for PC synthesis or the GPC-PDE pathway for GPC removal, for maintaining choline metabolite levels, or that sub-cellular sequestration of different phospholipase-mediated metabolic pathways are such that choline metabolite levels are not affected. However, even given this possibility, a combination of microscopy, kinetic data, inhibitor studies and isolation of products, enable reasonable estimates of the sub cellular localization as well as the type of phospholipase activated. Importantly, these data provide valuable information that allows selection of the most suitable probe(s) for animal studies.

Example 15: Demonstration of In Vivo Delivery, Bio-Distribution and Subsequent Activation of Phospholipases in Tumor Xenograft Models of Prostate Cancer and Non-Hodgkin's Lymphoma, Followed by Dual Modality Molecular Imaging Using $^1$H and $^{31}$P Mr Spectroscopy and Optical Imaging As a first step, phospholipase activity is imaged to assess the contributions of these enzymes to the increased PC levels observed during tumor progression and the increased GPC levels observed in response to chemotherapeutic agents. The data have shown that the prototype permanently fluorescent probe, Pyro-PL, is well tolerated by mice. It was demonstrated that in vivo optical imaging can be used to assess bio-distribution of these probes and that tumor localization of Pyro-PL does occur after intravenous injection. Moreover, it was demonstrated that in vivo activation of Pyro-PLBHQ is possible after i.p. injection.

A tumor xenograft animal model derived from the human prostate cell line DU145 and the human Non-Hodgkin's lymphoma cell line WSU-DLCL2 is used. These models were chosen based on differences in their native choline levels and on the ability of selected anticancer drugs to induce changes in choline levels in these models. DU145 and WSU-DLCL2 cells are grown as xenografts in the flanks of nude and SCID mice respectively followed by i.v. injection with fluorophore and NIR optical imaging.

Mice are matched with respect to age and weight; tumors are matched with respect to size and time after tumor implantation.

Mice are imaged using NIR optical imaging. Mice are placed in the imaging chamber and initial background images taken. Following the initial image, the mice are given a tail vein injection of fluorophore or pro-fluorophore and optical images recorded as a function of time Images are taken immediately (1-3 min after injection, depending on signal to noise), then at 3-5 min intervals for the first half hour. Imaging continues hourly out to 8 h, with follow up imaging at 16-72 h. The precise timing depends on the experiment being performed. At the end of the experiment, the mouse may be sacrificed and the organs removed, weighed and placed into 24 well plates for ex vivo scanning Following ex vivo scanning, the organs are homogenized, extracted with chloroform:methanol and the extracts assayed for fluorescence in 96-well plates on the fluorescent plate reader. Total fluorophore concentration (uncleaved pro-fluorophore and enzymatically released Pyro) is estimated by measuring absorption at 418 nm and calculated using Beer's law. Cleaved fluorophore concentration is estimated by fluorescence emission and comparison with a standard curve. In organ extracts where sufficient fluorescence is observed, the samples are retrieved and submitted for analysis using HPLC MALDI-TOF mass spec.

Cohorts of five matched mice are injected with sc tumors on their flanks for each of the tumor types DU145 and DLCL2. The number of cohorts employed depends on the number of fluorophores tested, the fluorophore concentrations used and the method of fluorophore dispersion. Maximum of four fluorophores at three concentrations plus saline matched control using two methods of dispersion are utilized. Thus there are a maximum of 32 conditions at 5 mice per cohort. Bio-distribution is measured using the permanently fluorescent phospholipid probes, where the fluorophore is attached to the phospholipid backbone in the absence of the quencher. Up to four permanent fluorophores are used to test, varying in the length of the linking spacer on the sn-2 position of the glycerol backbone. Tween-80 is an effective vehicle for the in vivo administration of Pyro-based NIR fluorophores. Optical imaging is performed at regular intervals out to 72 h as described above, depending on the duration of fluorescence intensity observed. From these data, the pharmacokinetics are obtained for the distribution of the probes to the tumor and other organs, as well as suitable concentrations for further experiments. Three bio-distribution curves are plotted from these data—that measured directly from in vivo data, taken from ex vivo organ imaging or determined from organ extracts. Since in vivo pharmacokinetic data is expected to be relatively crude due to the light scattering leading to imprecise localization, it is necessary to sacrifice cohorts of mice at multiple time points to measure detailed organ bio-distribution curves. These data fits to a biexponential pharmacokinetic equation, thus yielding detailed information on the fluorophore organ kinetics distribution. Bio-distribution is measured using the permanently fluorescent phospholipid probes, where the fluorophore is attached to the phospholipid backbone in the absence of the quencher varying in the length of the linking spacer on the sn-2 position of the glycerol backbone. Micellar delivery systems, such as Tween-80, are effective vehicles for the in vivo administration of Pyro-based NIR fluorophores. Optical imaging is performed at regular intervals out to 72 h as described above, depending on the duration of fluorescence intensity observed. From these data, the pharmacokinetics are obtained for the distribution of the probes to the tumor and other organs, as well as suitable concentrations for further experiments. Three bio-distribution curves are plotted from these data—that measured directly from in vivo data, taken from ex vivo organ imaging or determined from organ extracts. These data are fit to a biexponential pharmacokinetic equation, thus yielding detailed information on the fluorophore organ kinetics distribution.

Example 16: Monitoring Tumor Progression

Tumor-bearing animal models are used as described above treated with agents known to affect tumor growth and induce changes in choline metabolites. Fluorophores sensitive to the actions of PLA2 and PLC are used. In vivo $^1$H and $^{31}$P MRS can be used to monitor changes in choline metabolites during tumor growth and in response to therapy, and correlate this with the activation of phospholipase fluorophores.

In these experiments, mice are sequentially imaged using MRI/MRS followed by injection of phospholipase-activated probe and subsequent NIR imaging. Tumors are imaged at multiple time points throughout the growth of the xenograft, which is about 4 weeks. Sequential MRI/MRS and NIR imaging with re-injection of NIR pro-fluorophore are performed every 5-7 days. For each fluorophore sensitive to either PLA2 or PLC, three cohorts of six matched mice are imaged. One cohort is served as a sham-treated control. Two cohorts each would receive i.v. injections of the activatable fluorophores prepared in Tween or liposomes. Levels of choline metabolites are measured from MR spectra and compared to activation of NIR phospholipase beacons as measured by optical imaging. At the end of the experiment, the mice are sacrificed. In half of each cohort, the organs are removed for ex vivo optical imaging and extraction as described above. In the other half of each cohorts, tumors are freeze clamped, extracted with perchloric acid and choline metabolite levels assessed from high-resolution $^{31}$P and $^1$H MRS. Thus each fluorophore tested would required 18 mice per strain, assuming that statistically significant extract data is obtained from three mice. In addition, time points are identified during these experiments where tCho or PC levels are elevated in conjunction with increased enzymatic activity, as measured by the fluorescence released by the phospholipase-activated NIR beacons. In this case, a terminal experiment is performed.

Example 17: Monitoring Response to Therapy

This example describes an attempt to simultaneously monitor response to chemotherapy using MRS and NIR optical imaging. Six cohorts of six matched mice are employed for each tumor type, DU145 and DLCL2. Tumors of size range 200-400 µl are used. Two cohorts serve as sham-treated controls. Two cohorts are treated with a therapeutic dose of phenylbutyrate (300-500 mg/kg/day, i.p.), two cohorts are treated with a therapeutic dose of cyclophosphamide (300 mg/kg i.p.). One cohort from each group receives i.v. injections of NIR phospholipase beacons. Proton MR images and spectra are measured the day before treatment, 4-6 h after the initiation of treatment, 1 day after treatment and then every second day after treatment (days 3, 5, 7, and 9). NIR fluorophores are injected 1 h after treatment and assessed as described above, with second injections as necessary. Shorter imaging time periods are being used in these experiments to assess the acute effects of cytotoxic agents.

Having described preferred embodiments of the invention with reference to the accompanying drawings, it is to be understood that the invention is not limited to the precise embodiments, and that various changes and modifications may be effected therein by those skilled in the art without departing from the scope or spirit of the invention as defined in the appended claims.

What is claimed is:

1. A method of analyzing a sample for the presence of a phospholipase, the method comprising:
   contacting a sample suspected of comprising a phospholipase with a phospholipid-based near infrared (NIF) molecular beacon comprising (i) a phospholipid moiety with a glycerol backbone; (ii) a first fluorophore moiety covalently linked to the glycerol backbone either directly or via a linker, wherein said first fluorophore moiety is an NIR fluorophore moiety; and (iii) a fluorescence quencher moiety covalently linked to said phospholipid glycerol backbone either directly or via a linker, wherein the fluorophore moiety, the fluorescence quencher moiety or both are uncharged when covalently linked at either or both sn-1 or sn-2 fatty acyl positions; and detecting the NIR fluorescence of said NIR fluorophore moiety as a function of time, wherein an increase in the NIR fluorescence as a function of time correlates with the presence of the phospholipase in the sample.

2. The method of claim 1, wherein said NIR fluorophore is covalently bound to the glycerol backbone at either the sn-1 or sn-2 fatty acyl positions or to the sn-3 head group.

3. The method of claim 2, wherein said quencher moiety is a second fluorophore covalently bound to the remaining unbound fatty acyl position or the sn-3 head group.

4. The method of claim 3, wherein said second fluorophore moiety or quencher moiety is covalently linked to the phospholipid moiety either directly or via a linker.

5. The method of claim 1, wherein said sample is a tumor cell or an extract of a tumor cell.

6. The method of claim 1, wherein said sample is a cultured cell, a primary cell culture or their combination.

7. A method of monitoring the activity of a phospholipase in vivo, comprising the steps of:
   exposing a tissue to a phospholipid-based near infrared (NIR) molecular beacon under conditions effective to permit said phospholipase to cleave said beacon, wherein said beacon comprises (i) a phospholipid moiety with a glycerol backbone; (ii) a first fluorophore moiety covalently linked to the glycerol backbone either directly or via a linker, wherein said first fluorophore moiety is an NIR fluorophore moiety; and (iii) a fluorescence quencher moiety covalently linked to said phospholipid glycerol backbone either directly or via a linker, wherein the fluorophore moiety, the fluorescence quencher moiety or both are uncharged when covalently linked at either or both sn-1 or sn-2 fatty acyl positions; and detecting the fluorescence of said fluorophore moiety as a function of time, wherein an increase in the quantity or rate of accumulation of fluorescence as compared to a control reaction identifies the activity of the phospholipase.

8. The method of claim 7, wherein said NIR fluorophore is covalently bound to the glycerol backbone at either the sn-1 or sn-2 fatty acyl positions or to the sn-3 head group.

9. The method of claim 8, wherein the quencher moiety is a second fluorophore covalently bound to the remaining unbound fatty acyl position or the sn-3 head group.

10. The method of claim 9, wherein said second fluorophore moiety or quencher moiety is covalently linked to the phospholipid moiety either directly or via a linker.

* * * * *